United States Patent [19]
Hu et al.

[11] Patent Number: 6,022,558
[45] Date of Patent: Feb. 8, 2000

[54] TRANSDERMAL PREPARATIONS OF OXICAMS

[76] Inventors: Oliver Yoa-Pu Hu, No, 18 Sih-Yuan St., Taipei 100; Chieh Fu Chen, No, 155-1, Sec 2, Li Nung St, Taipei, both of Taiwan

[21] Appl. No.: 08/886,400

[22] Filed: Jul. 1, 1997

[51] Int. Cl.[7] .................................................. A61F 13/00
[52] U.S. Cl. ........................... 424/449; 514/946; 514/947; 514/944; 514/969
[58] Field of Search .............................. 424/449; 514/946, 514/947, 944, 969

[56] References Cited

U.S. PATENT DOCUMENTS 5,120,546  6/1992  Hansen ..................................... 424/449
5,340,568  8/1994  Piazza ....................................... 424/59
5,505,956  4/1996  Kim ......................................... 424/449

*Primary Examiner*—D. Gabrielle Brouillette
*Attorney, Agent, or Firm*—Jacobson, Price, Holman & Stern, PLLC

[57] ABSTRACT

The present invention is related to a trandermal preparation of oxicams. In preparation, it is comprised of 0.1% to 50% of an oxicam, 0.1% to 70% of pure compositions from Chinese herbal enhancers as enhancers, as well as other necessary excipients for transdermal delivery of an active ingredient. This transdermal preparation is intended to be used for anti-inflammatory cases, but with few gastrointestinal side effects. Based on results from testing this preparation on nude mice skin, rabbit skin, and human leg skin, it was found that skin penetration of the transdermal preparation containing 20% terpineol oil was 157.6 times higher than that of the control group.

16 Claims, 30 Drawing Sheets

Fig 1(A)
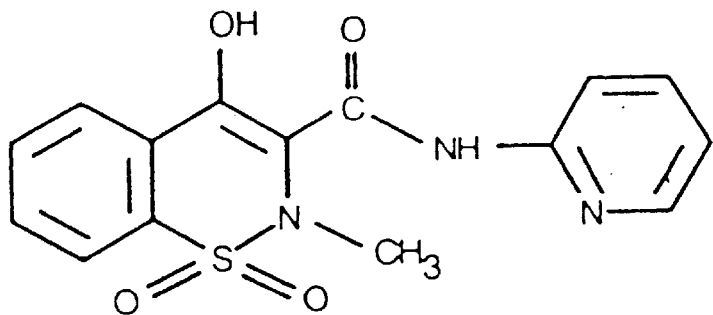
Piroxicam
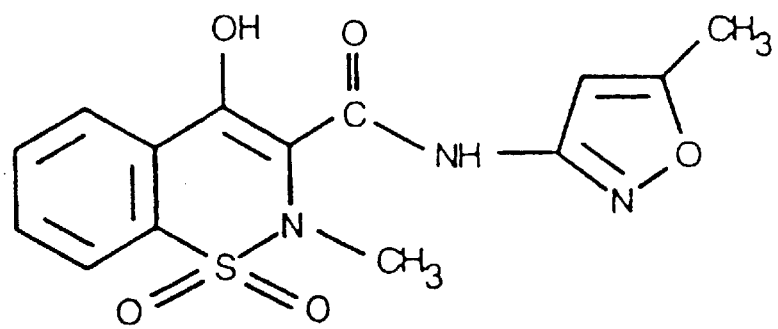
Isoxicam
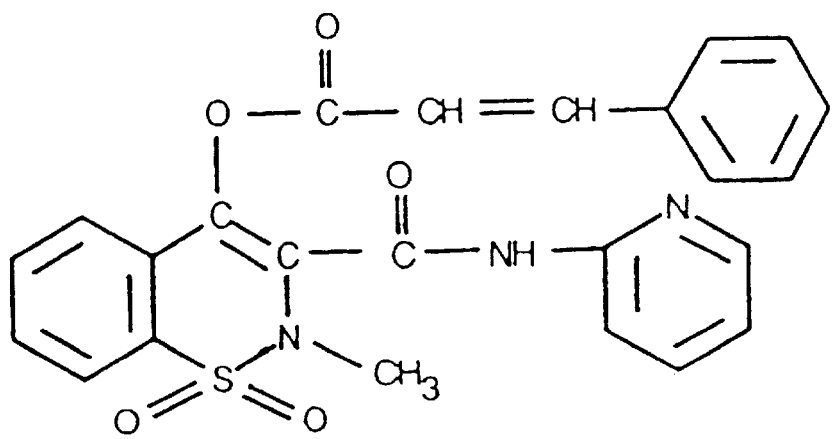
Cinnoxicam

Fig 1(B)
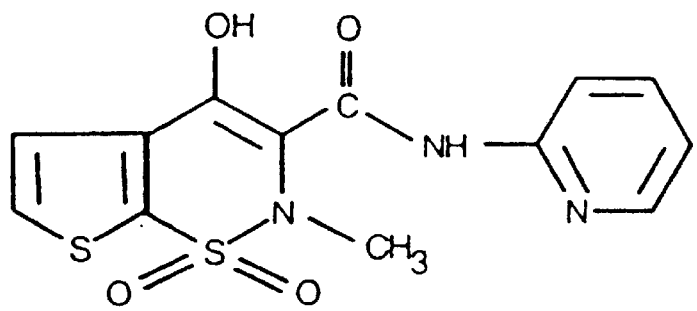
Tenoxicam
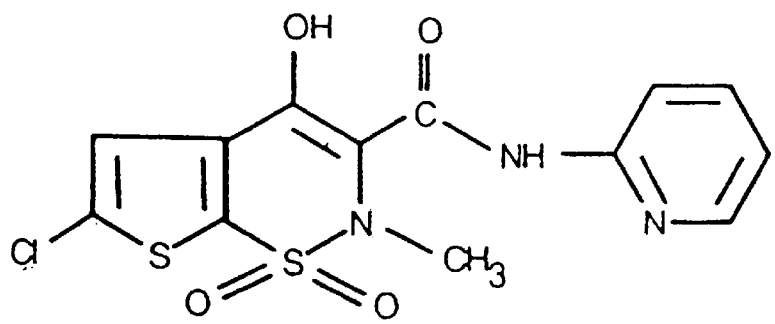
Lornoxicam
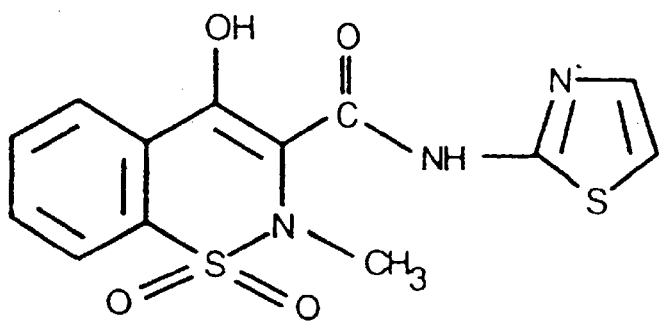
Sudoxicam

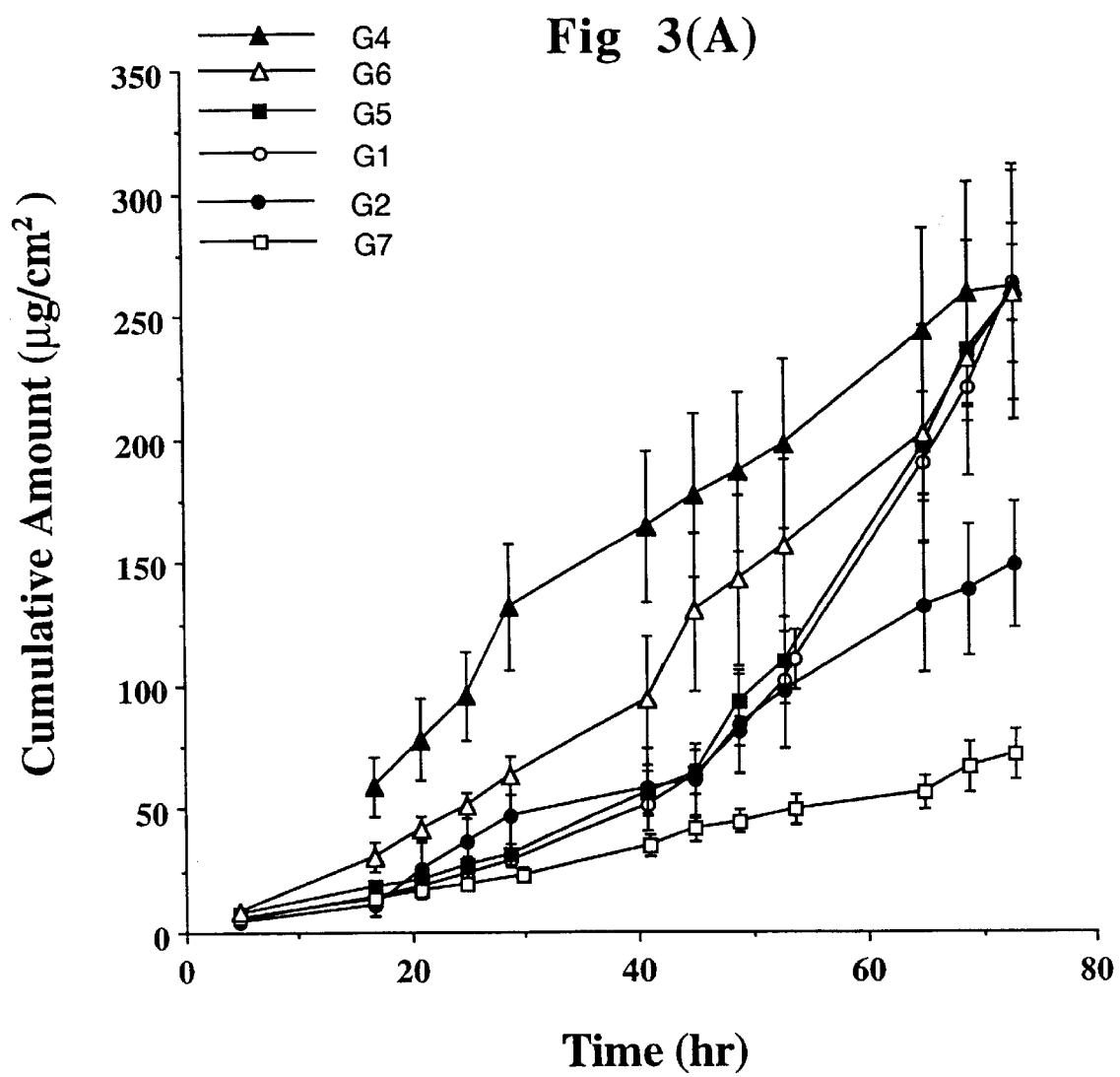

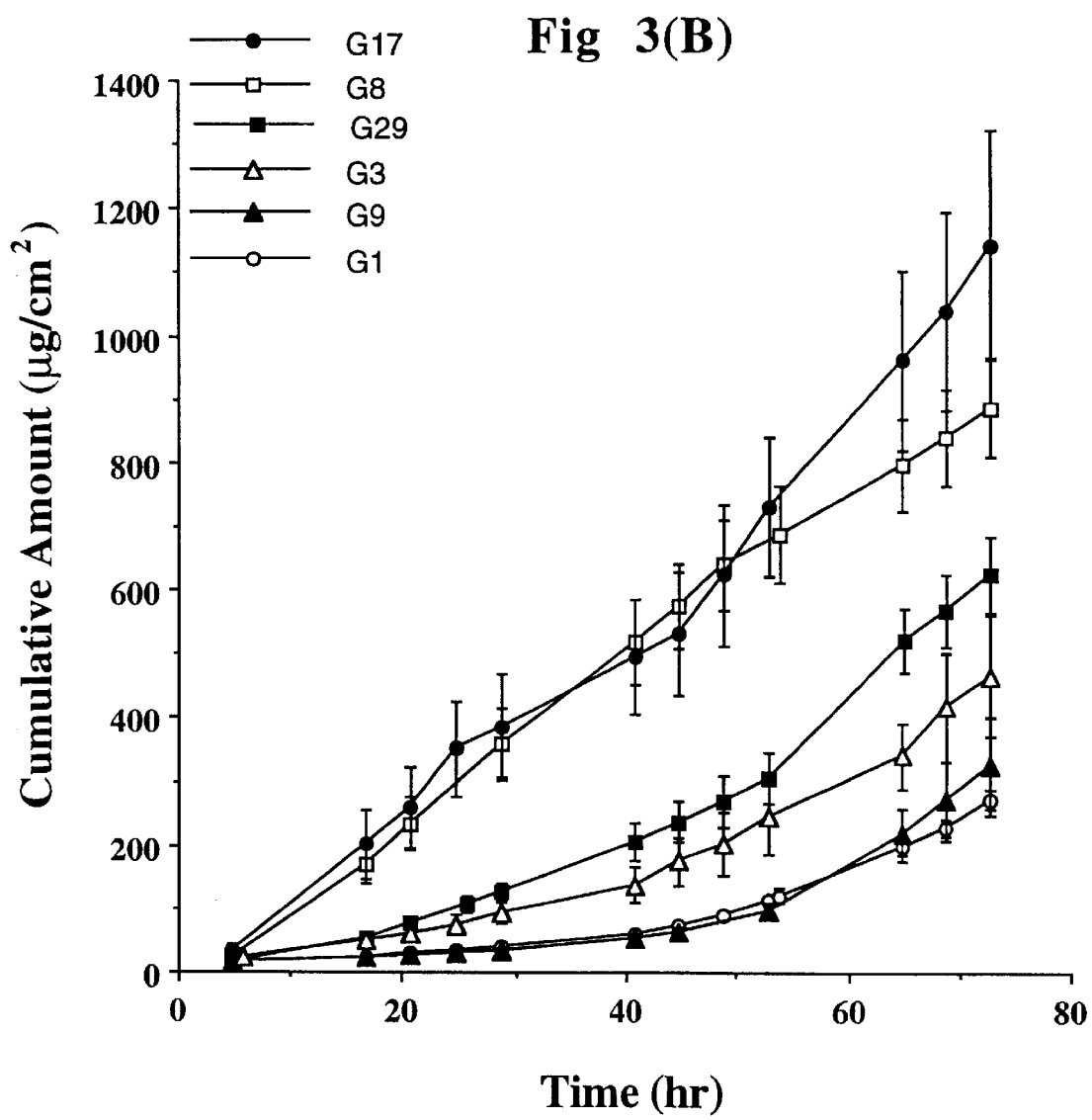

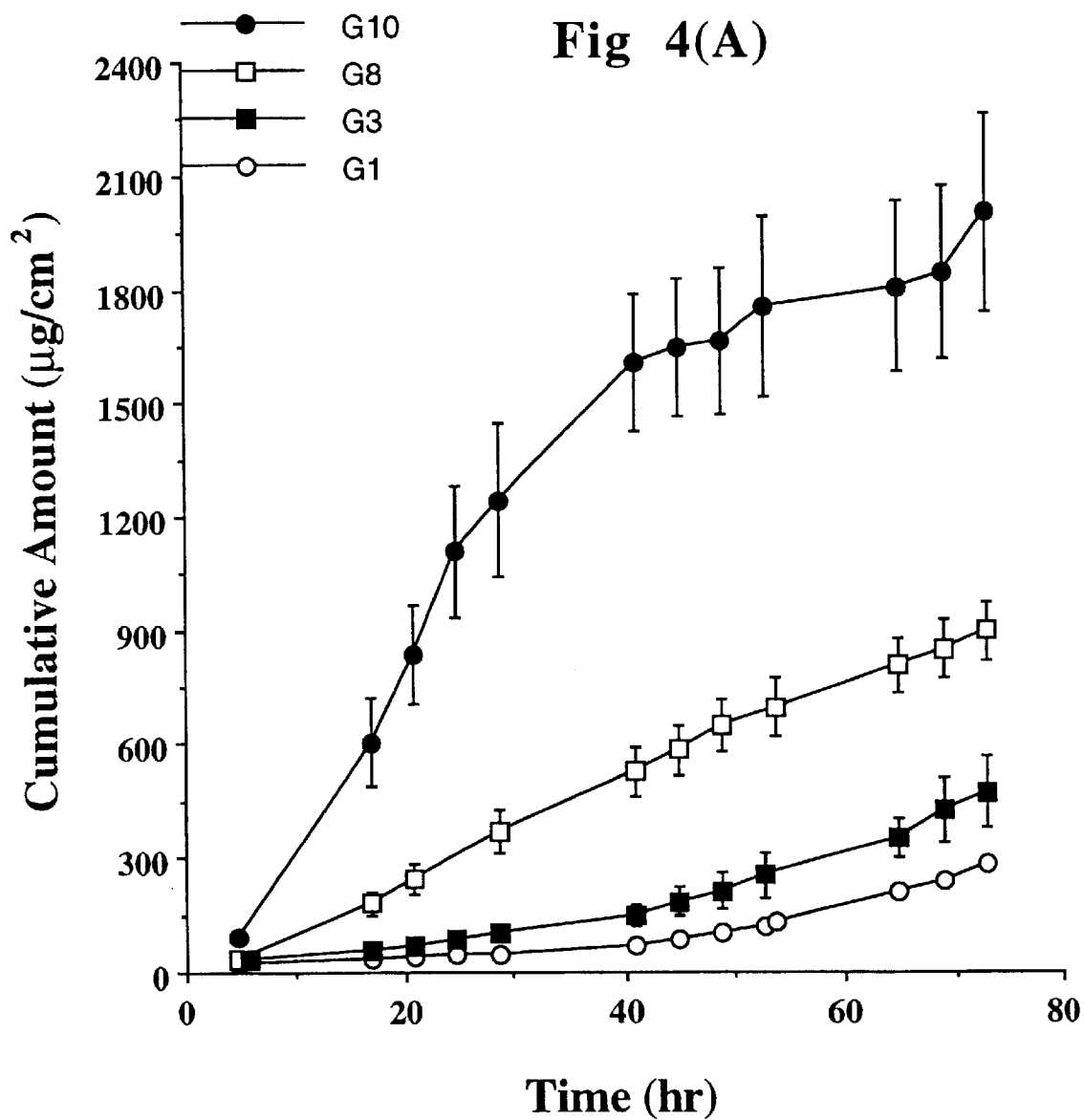

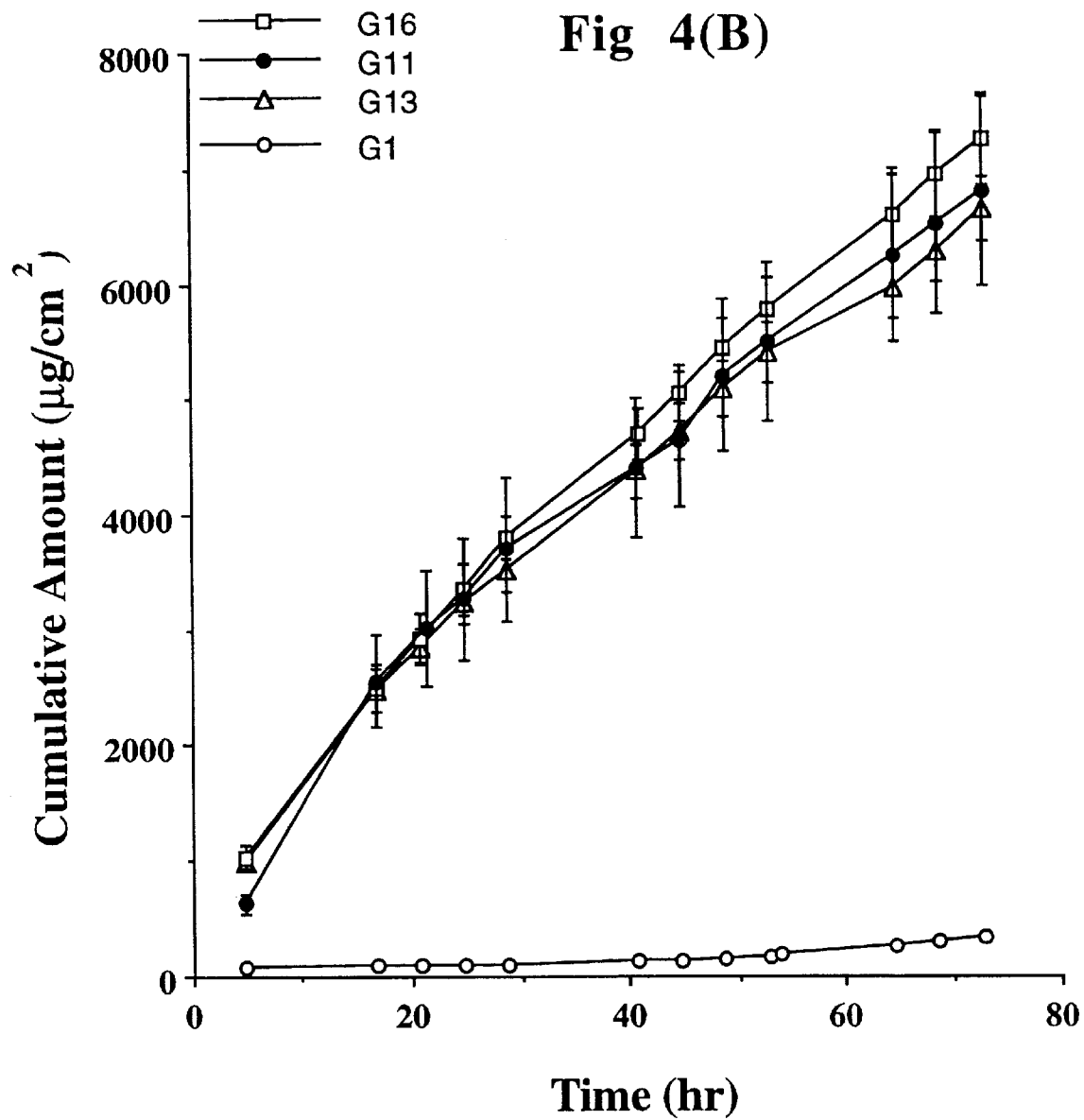

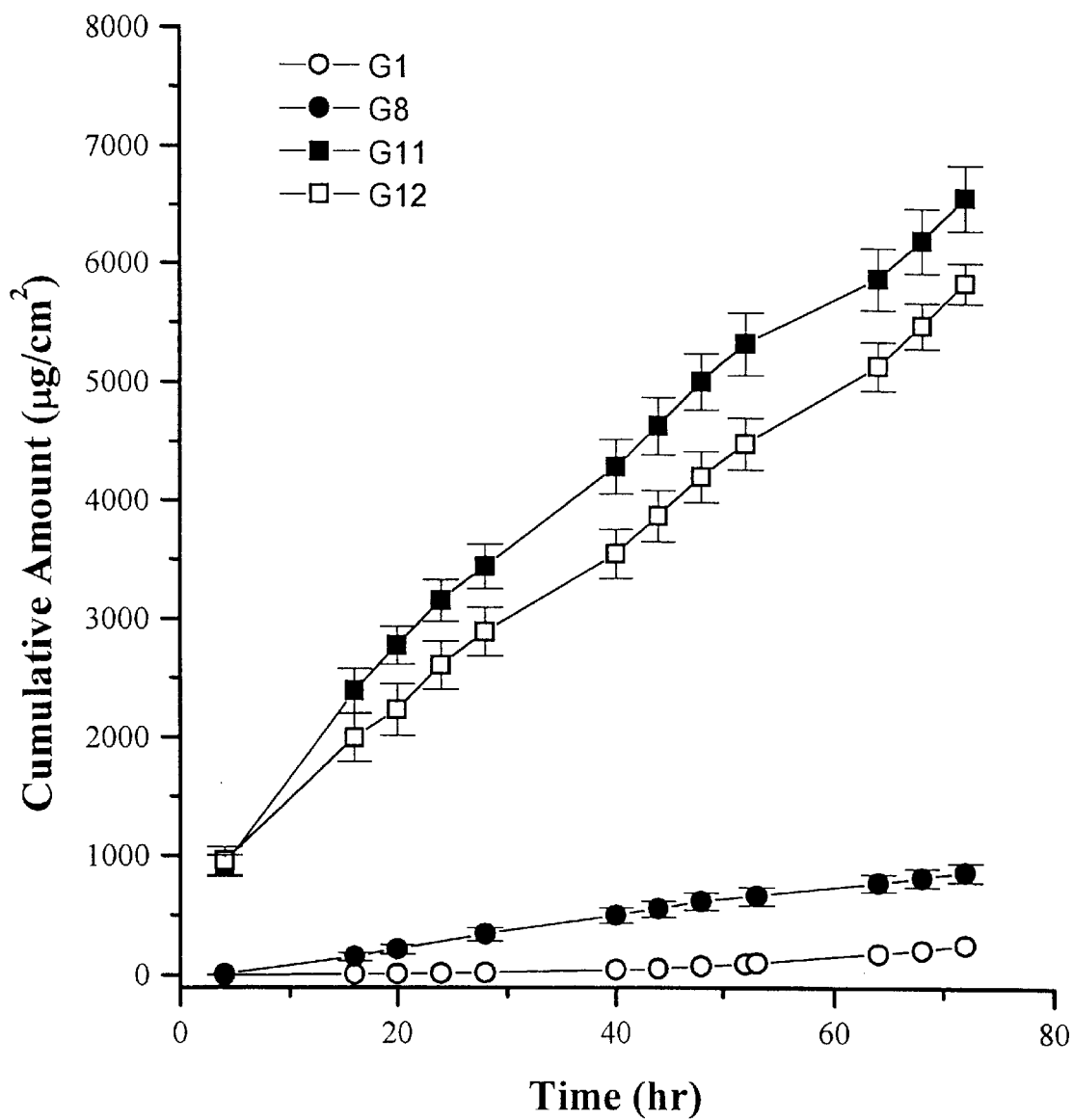

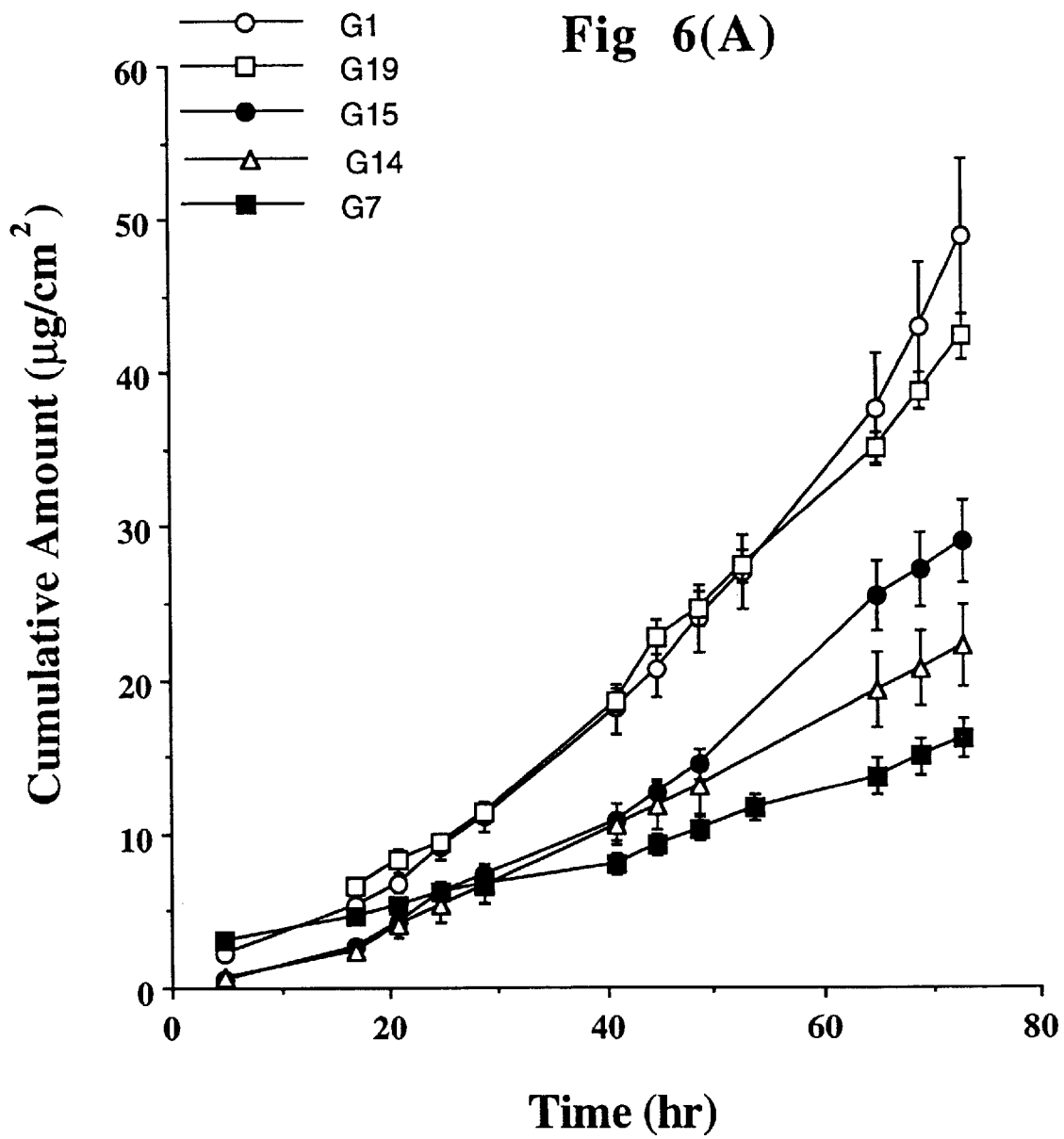

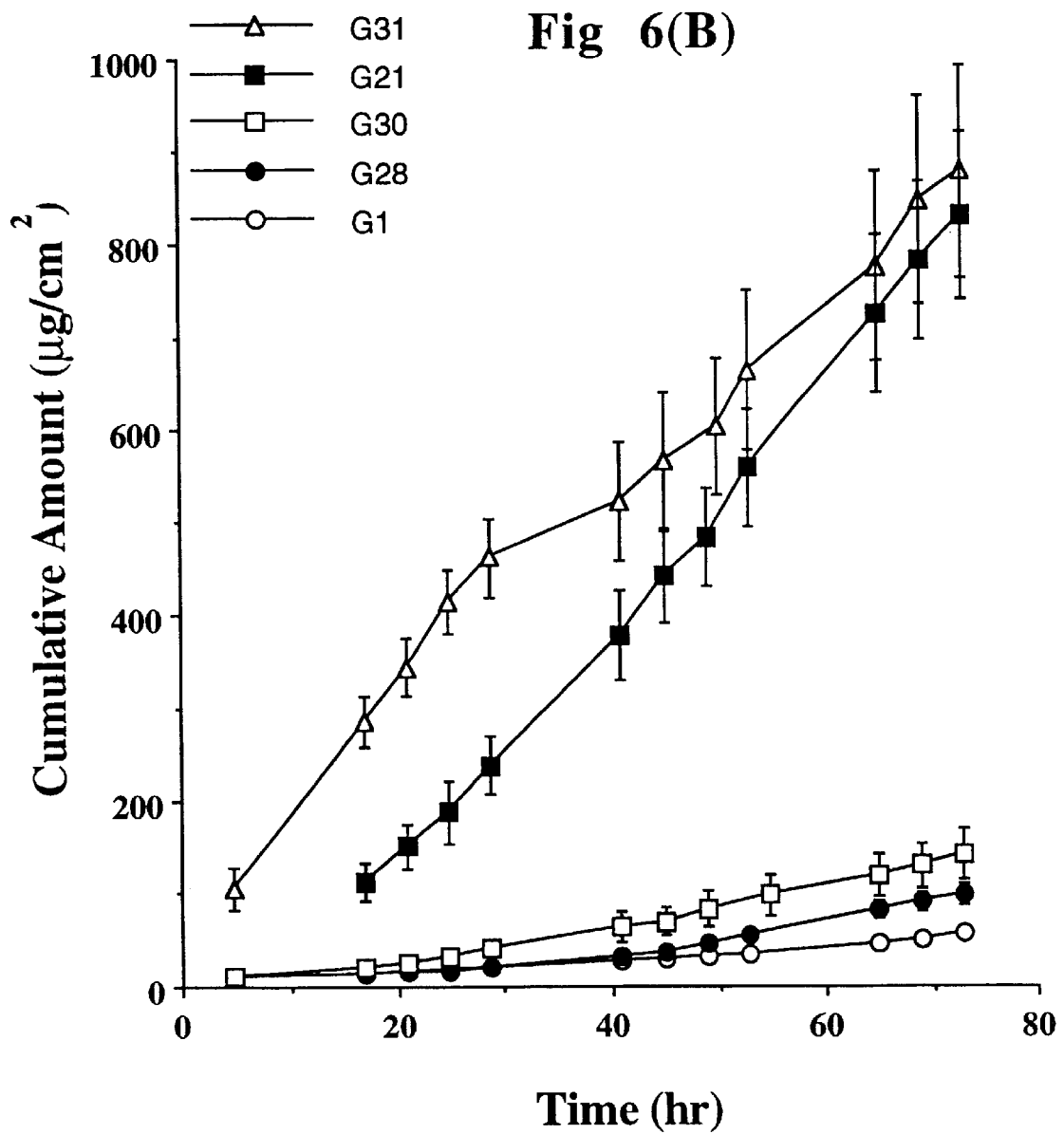

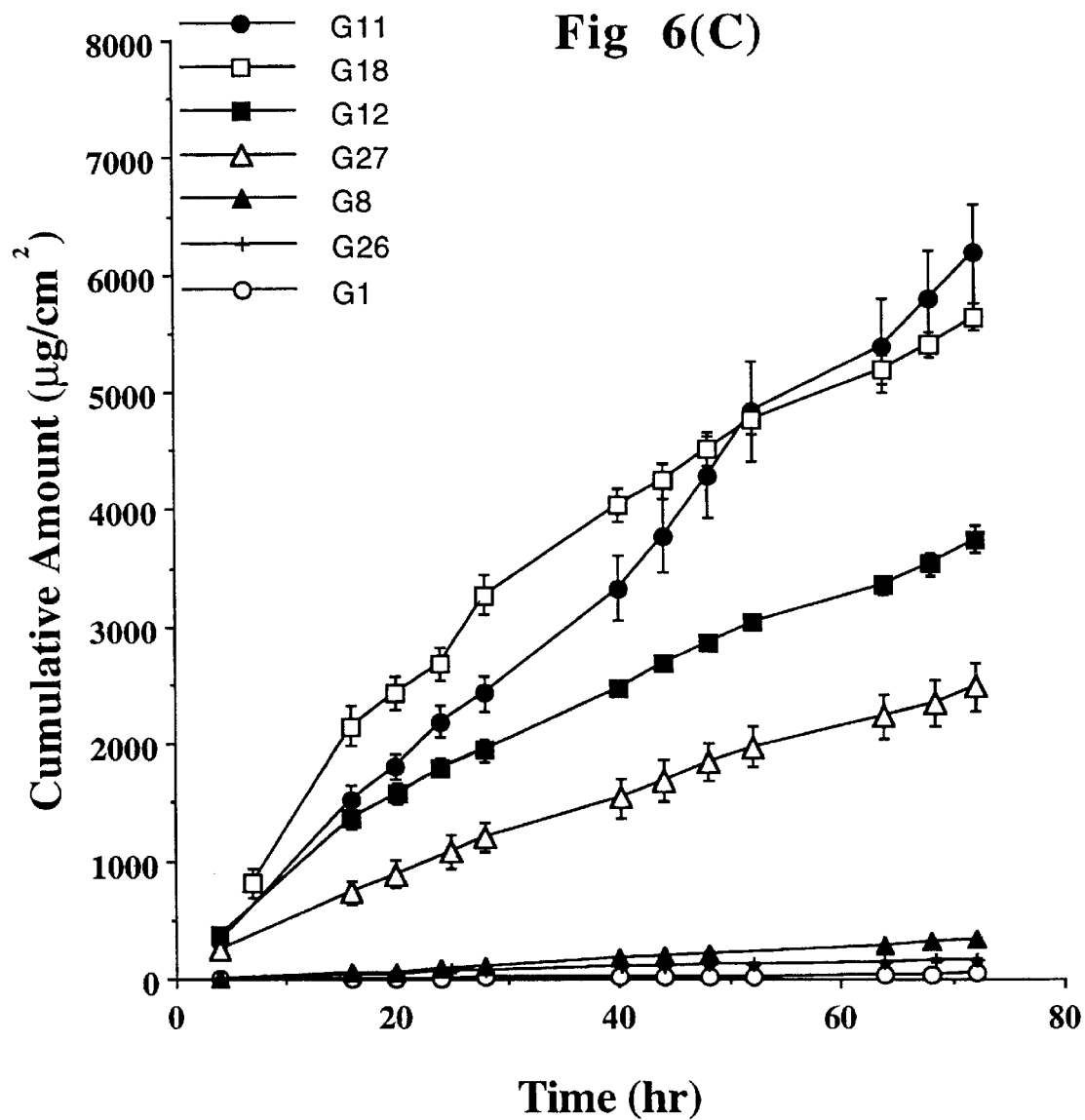

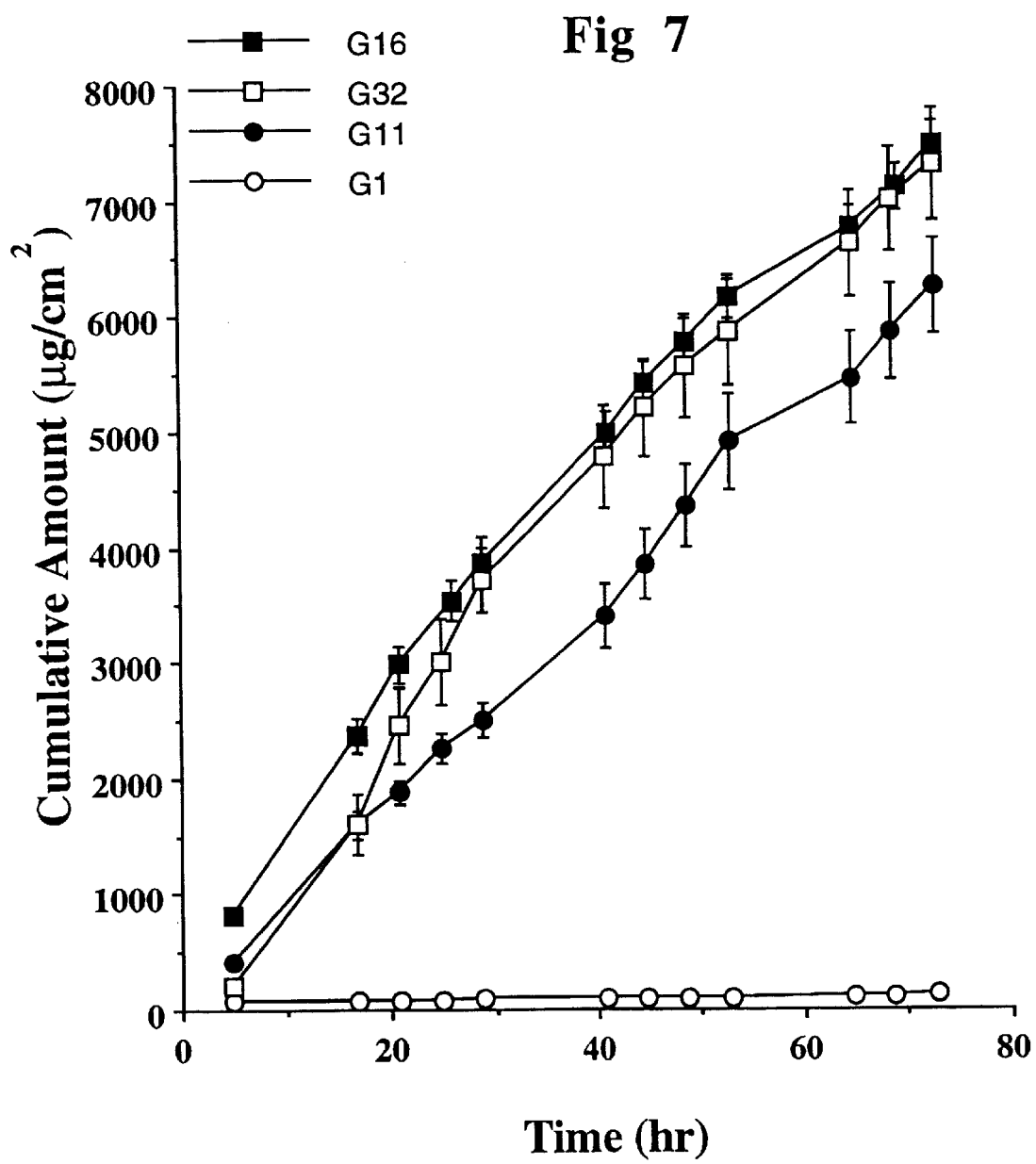

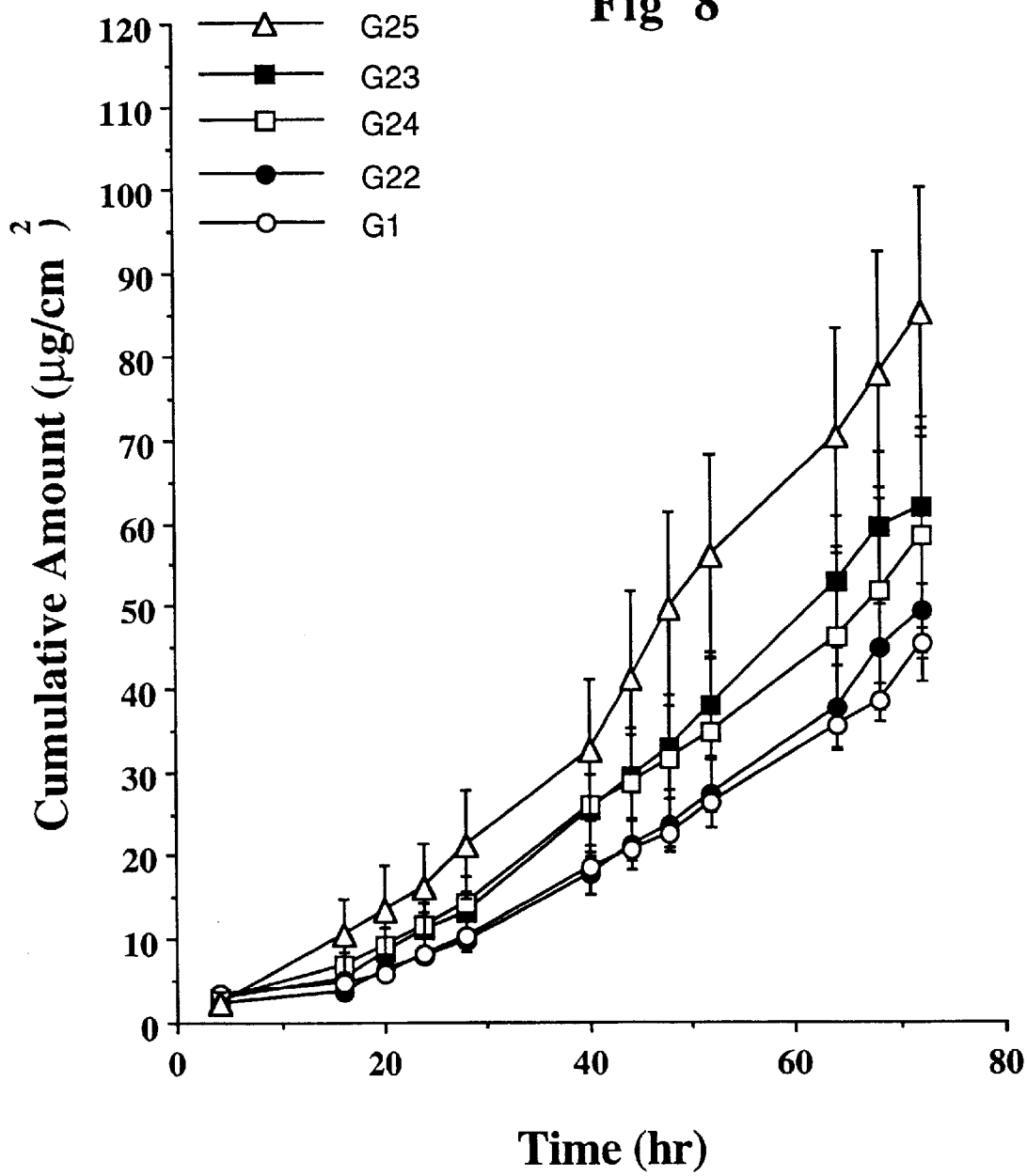

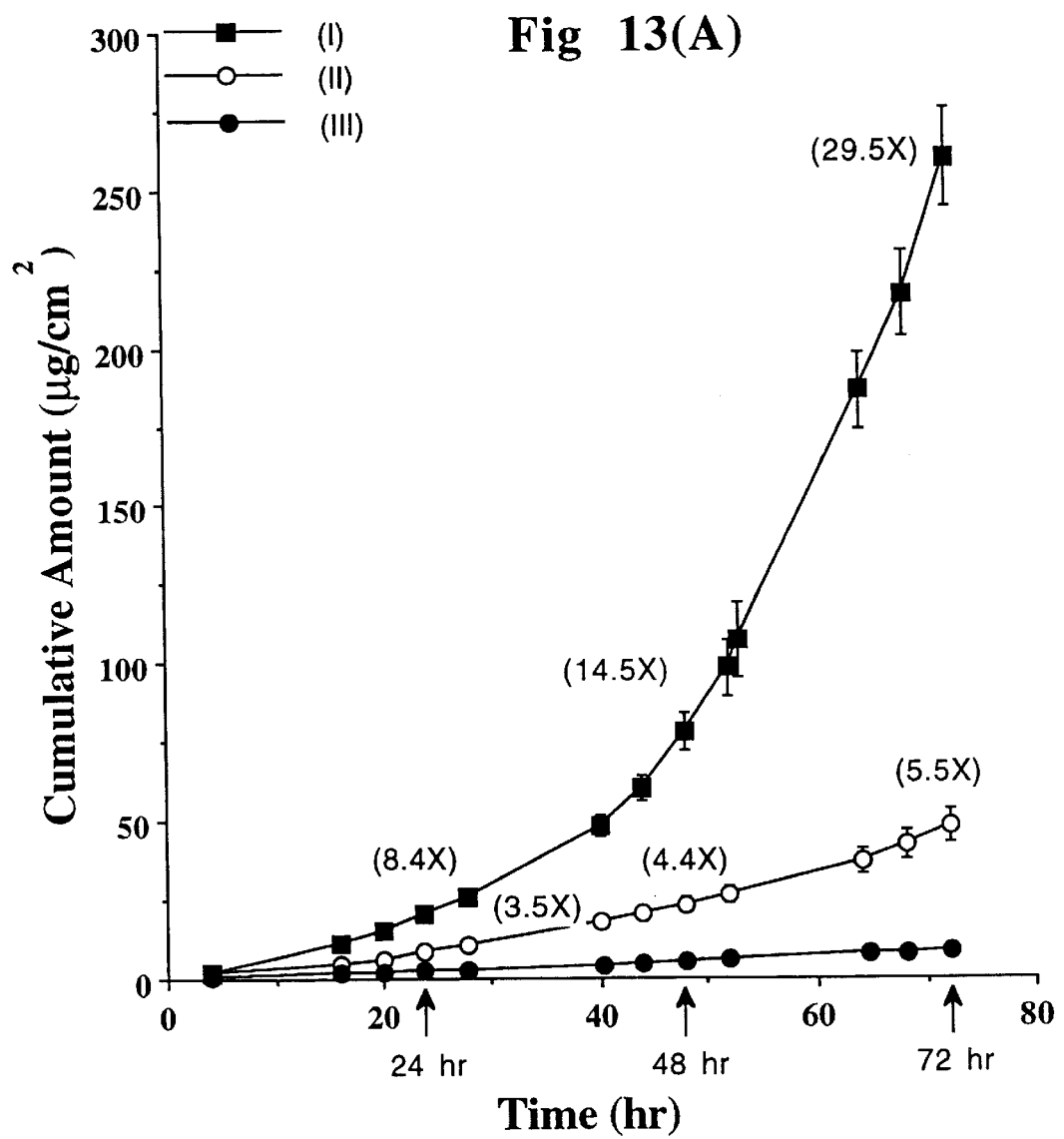

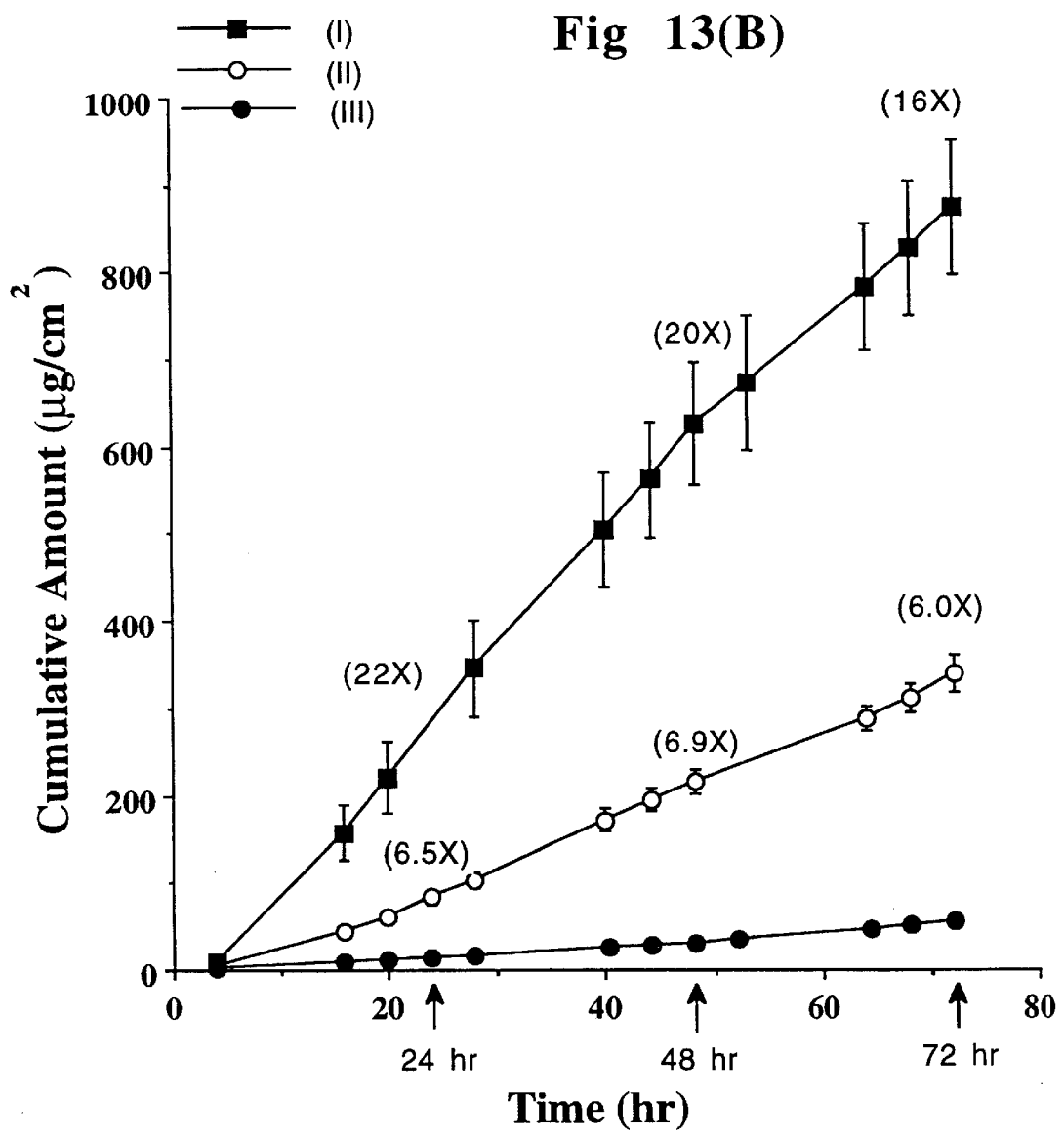

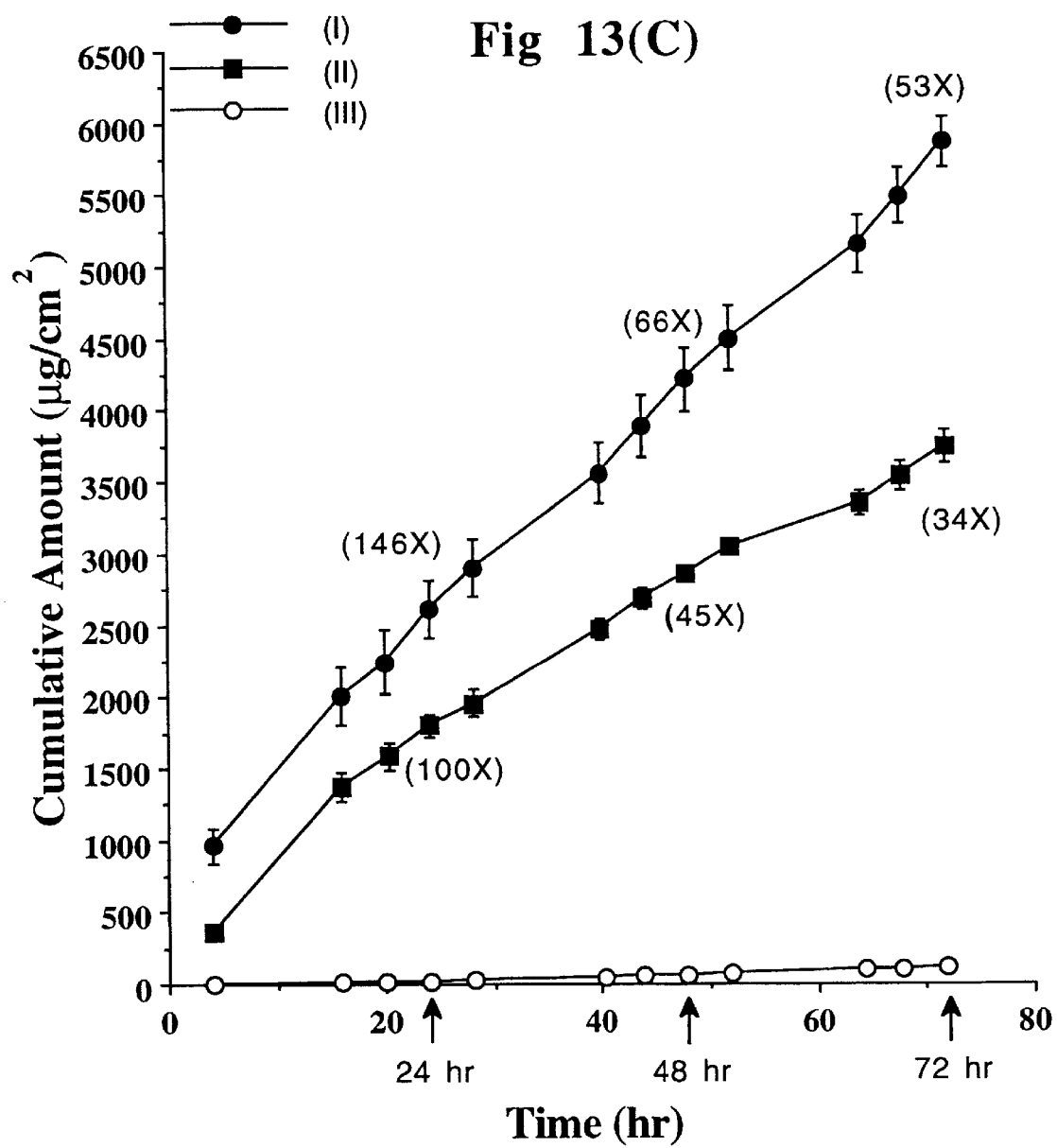

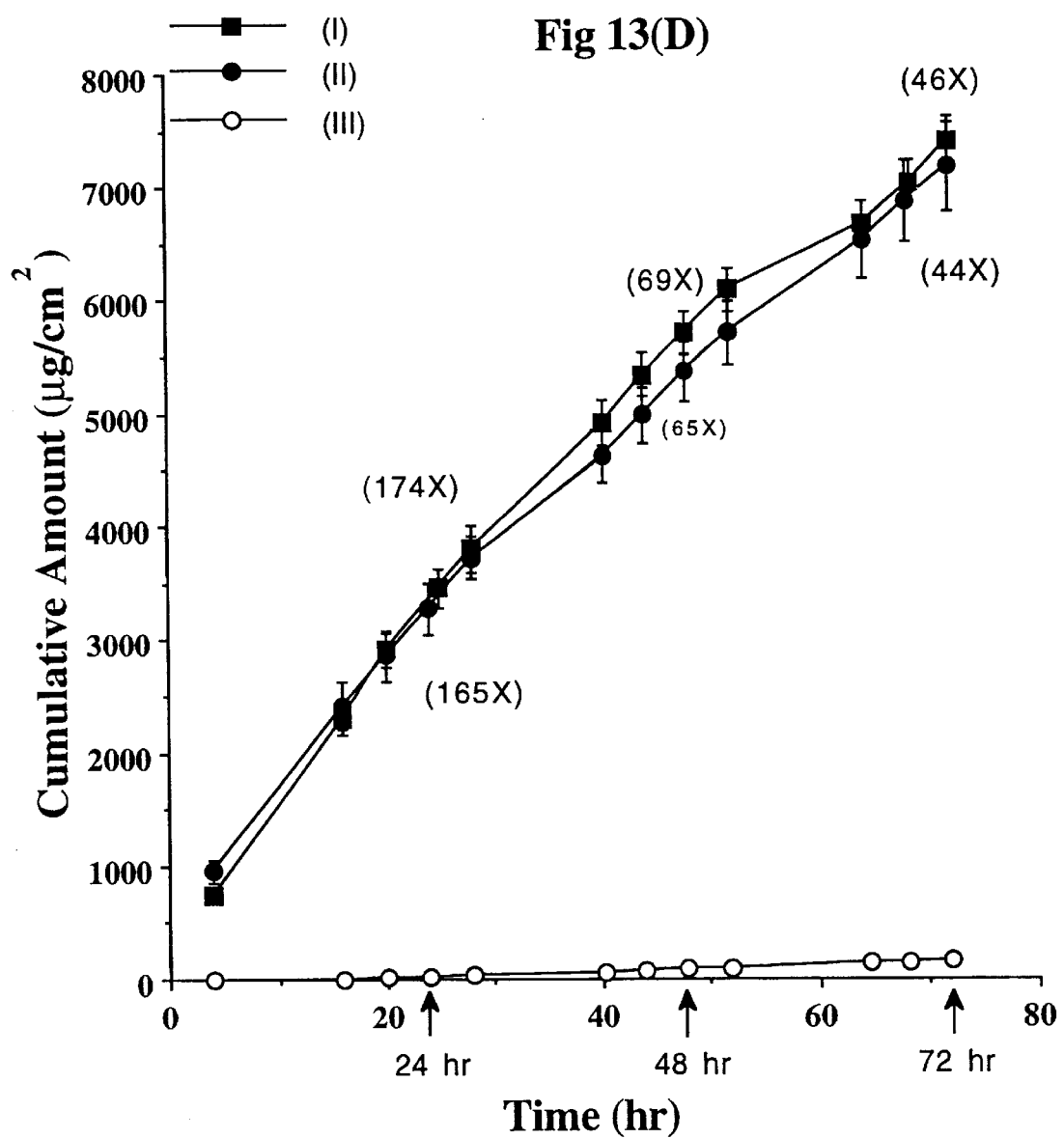

TRANSDERMAL PREPARATIONS OF OXICAMS

BACKGROUND OF THE INVENTION

At the present time, non-steroidal anti-inflammatory drugs are comprised of two categories, one the carboxylic acid, and the other enolic acid. Carboxylic acid type non-steroidal anti-inflammatory drugs are easily metabolized in the body, or conjugated with glucuronic acid and promptly excreted in the urine, resulting in a short half-life. Among this type of non-steroidal anti-inflammatory drugs, whose structures containing oxicam are easily absorbed, but hepatic metabolism and renal clearance are slower. Piroxicam(4-hydroxyl-2-methyl-N-(2-pyridyl)-2H-1,2-benzo-thiazine-3-carboxamide-1,1-dioxide) belongs to this category, and its side effect is long recognized to be less than other non-steroidal anti-inflammatory drugs in the same category. In addition to piroxicam, other oxicams include isoxicam, sudoxicam, cinnoxicam, tenoxicam, and lomoxicam. They have anti-inflammatory, anti-pyretic and analgesic effects, but do not have typical side effects of narcotic analgesic drugs, such as breath suppression, and addiction. Therefore, these non-steroidal anti-inflammatory drugs are classified as non-narcotic analgesies. Non-steroidal anti-inflammatory drugs are extensively used in clinical treatment, since they can relieve mild to moderate pain, lower body temperature, reduce inflammatory symptoms, and prevent or relieve gout.

According to reports revealed by Brogden R. N. et al. in 1981 *Drugs,* volume 22, page 165 to 187, piroxicam possessed a linear pharmacokinetic property. Regardless of whether single or multiple doses were administered to patients, the maximum plasma concentration(Cmax) and area under the curve(AUC) are proportional to the dose administered. Results from experiments of the oral, rectal, and intravenous routes in rats and rabbits showed that oral administration of piroxicam was almost completely absorbed. Since piroxicam is a weak acid, it is in the non-ionized form while in the stomach. According to reports by Benveniste C. et al. revealed in 1985 *Eur. J. Clin. Pharmacol.* volume 38, page 547 to 549, oral administration of piroxicam shows a maximum plasma concentration after two hours, and then shows a second maximum plasma concentration due to hepatic and intestinal recycling.

In recent years, pharmaceutical development has focused on dosage forms that could bypass the gastrointestinal tract and liver, in order to avoid the first pass effect, or gastrointestinal side effects. Meanwhile the plasma concentration could be constantly maintained. Among these dosage forms, a transdermal delivery system has been shown to release the drug constantly, and delivers it into capillary vessels upon penetration through the skin, resulting in reaching the target area and producing a therapeutic effect. In addition, a transdermal drug delivery system is more convenient than other dosage forms, since the patch can be removed at any time, which may avoid emergency situations due to dose dumping. For an adult, the total area of the skin is 2 $m^2$, and capillary vessels possess one third of blood flow. For these reasons, transdermal drug delivery system has a potential future.

For transdermal drug delivery, physical-chemical properties of drug such as partition coefficient, molecular weight, size, concentration, and polarity may affect the result of delivery. Other factors such as polarity of transdermal base, solubility of drug in the transdermal base, compositions in the base, viscosity, pathologic and physiological conditions of the skin: hydration condition, and skin temperature, as well as the position of patch placement all may affect the result of drug delivery. However, the most difficult problem at the present time is the lack of potent and safe transdermal absorption enhancers.

One of the recent advances in oriental medicine was the fact that the Japanese Ministry of Health agreed in 1975 to include 210 Chinese herbal medicines in the nation-wide health insurance program. Among these, Glycyrrhizae Radix had the highest rate of usage, 71.4%. Others in descending rank were: Zingiberis Rhizoma 42.9%, Hoelen 35.2%, Paeoniae Radix 32.9%, Zizyphi Fructus 31.9%, and Cinnamoni Cortex et Caulis 29.5%. In the second edition of the Japanese National Formulary, the highest rate of usage remained Glycyrrhizae Radix, the second highest was Zingiberis Rhizoma, and others were similar to past usage.

In Chinese herb formulas, the following herbs have high frequencies of usage. They are Glycyrrhizae Radix, Enzoinum, Cinnamoni Cortex et Caulis, Zingiberis Rhizoma, Zizyphi Fructus, Zedoariae Rhizoma, Magnoliae Flos, Foeniculi Fructus, Cardamomi Fructus, Eucalypti Folium, Zanthoxylic Fructus, Lupuli Strobilus, Magnoliae Cortex, Cinae Flos, Perillae Herba, Valerianae Radix, Asari Herba cum Radice, Amomi Cardamomi Fructus, Myristicae Semen, Menthae Herba, Digitalis Folium, Benzonium, Corni Fructus, Piperis Fructus, Hoelen, Polyporus, Ergota, Ephedrae Herba, Platycodi Radix, Caryophylli Flos, Bufonis Venenum, Schizonepetae Herba, Citri Exocarpium, Aurantii Fructus Immaturus, Rhei Rhizoma, Arecae Semen, Gambir, etc.. The amount or composition of the natural products in these Chinese herbs may be varied due to the area where grown and seasons of harvest.

These herbs usually contain monoterpinoid glycosides, triterpinoid glycosides, triterpinoid saponins, tannin, and volatile oils. They are all bioactive. Triterpinoid glycosides may lower the surface tension of the skin, which helps drug to penetrate to deeper tissues, and results in higher therapeutic effects. Volatile oil, and glycyrrhizin are proven to have an anti-inflammatory effect. Furthermore, Glycyrrhizin can inhibit paw swelling.

SUMMARY OF THE INVENTION

The present invention employed pure Chinese herb medicine enhancer as a transdermal absorption enhancer. The transdermal preparation included an active ingredient(0.1 to 50%) possessing anti-inflammatory, and analgesic properties, and 0.1% to 70% of pure Chinese herb enhancer as transdermal absorption enhancer, as well as other necessary excipients for transdermal preparation.

The present invention "transdermal delivery of oxicams" included 0.1% to 50% of an anti-inflammatory agent, 0.1% to 70% of pure Chinese herb enhancer as transdermal absorption enhancer, and other necessary excipients for transdermal preparation. The percent of excipient was from 0.01% to 99.95%, containing a mixture of sodium carboxymethylcellulose and ethylene glycol. Preparations utilized the present invention included ointment, suspension, gel, solution, emulsion, lotion, paste, patch, aerosol, and other local preparations. The active ingredient was referred to anti-inflammatory agents whose structures were oxicams. Their structures were shown in FIG. 1, presenting as piroxicam, sudoxicam, tenoxicam, isoxicam, cinnoxicam, and lomoxicam. The better choices were piroxicam, isoxicam, and tenoxicam.

The invention will now be described by way of example with reference to the accompanying in which:

Table 1. Chinese herbs enhancers used as transdermal absorption enhancers

Table 2. Compositions of preparations

Table 3. Accumulated amount of penetration and kinetic parameters of porixicam on nude mice abdominal skin Table 4. Accumulated amount of penetration and kinetic parameters of piroxicam on rabbit abdominal skin Table 5. Accumulated amount of penetration and kinetic parameters of piroxicam on rabbit abdominal skin with different amounts of piroxicam Table 6. Accumulated amount of penetration and kinetic parameters of piroxicam on human leg skin Table 7(A)–7(B). Accumulated amount of penetration and kinetic parameters of piroxicam for four different preparations on various kinds of skin Table 7(A). pH 7.4 phosphate solution in receiver phase Table 7(B). 30% DMSO solution in receiver phase Table 8. Accumulated amount of penetration and kinetic parameters of oxicams for different oxicam drugs on rabbit abdominal skin

BRIEF DESCRIPTION OF THE DRAWINGS

FIG. 1. Structures of oxicam type of anti-inflammatory drugs

G16 . . . 20% terpineol(receiver phase was 30% DMSO)

Figure 10:
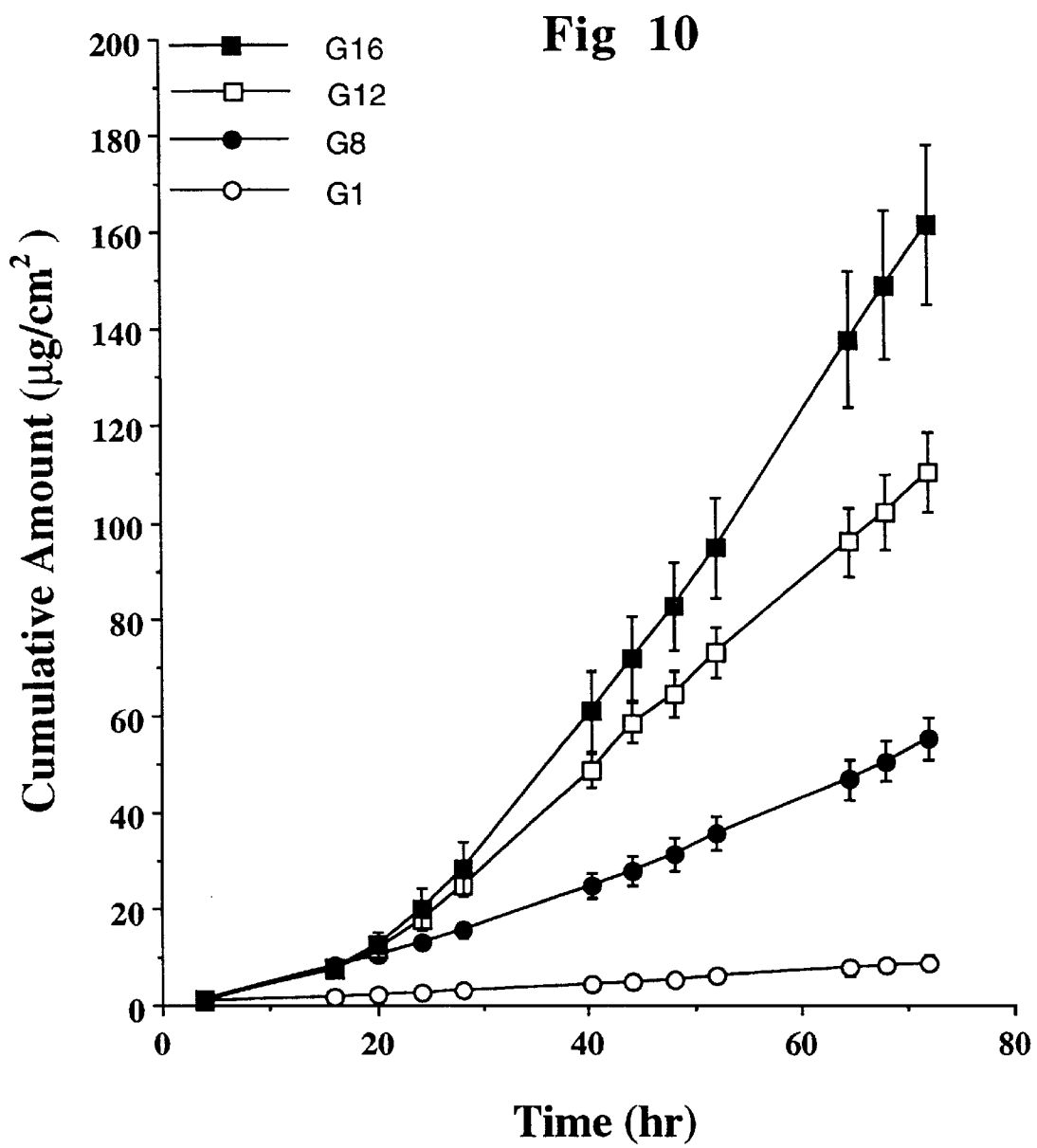

FIG. 10. Various concentrations of same pure Chinese herb enhancer tested on human leg skin G16 . . . 20% terpineol
G12 . . . 10% terpineol+10% β-myrcene
G8 . . . 10% β-myrcene
G1 . . . control FIG. 11. Formula containing 20% terpineol using different receiver phase tested on rabbit abdominal skin G1 . . . control(receiver phase was pH 7.4 phosphate buffer)
G16 . . . 20% terpineol(receiver phase was pH 7.4 phosphate buffer)
G1 . . . control(receiver phase was 30% DMSO)
G16 . . . 20% terpineol (accepting phase was 30% DMSO)

Figure 12:
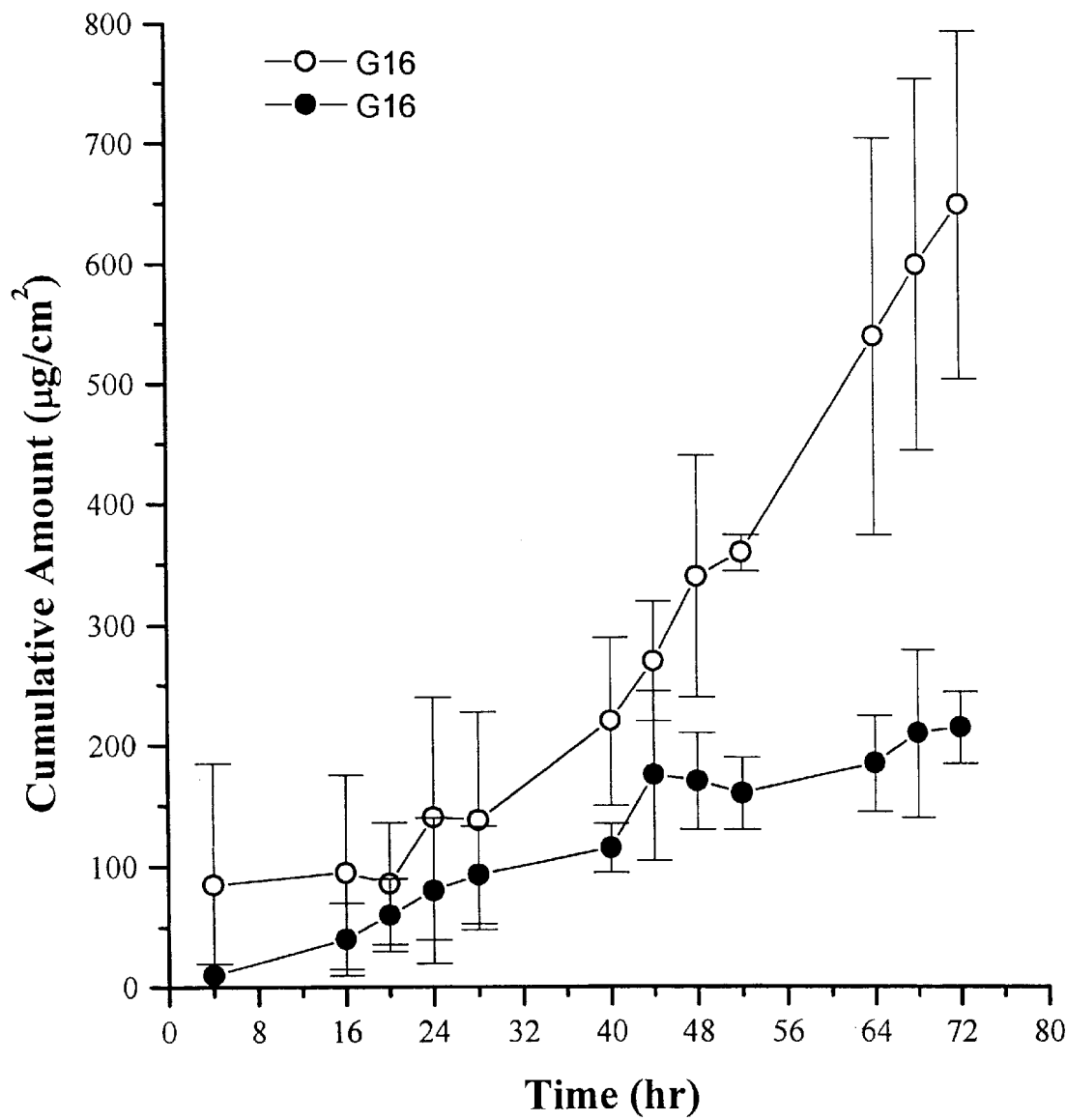

FIG. 12. Formula containing terpineol and DMSO tested on human leg skin for penetration G16 . . . 20% terpineol
G16 . . . 20% terpineol+20% DMSO FIGS. 13(A)–13(D). Piroxicam Penetration of four preparations on various skins FIG. 13(A). G1 formula
(I) nude mice abdominal skin
(II) rabbit abdominal skin
(III) human leg skin FIG. 13(B). G8 containing 10% β-myrcene
(I) nude mice abdominal skin
(II) rabbit abdominal skin
(III) human leg skin FIG. 13(C). G12 containing 10% β-myrcene+10% terpineol
(I) nude mice abdominal skin
(II) rabbit abdominal skin
(III) human leg skin FIG. 13(D). G16 containing 20% terpineol
(I) nude mice abdominal skin
(II) rabbit abdominal skin
(III) human leg skin FIGS. 14(A)–14(B). Penetration of two preparations on various skins (receiver phase was 30% DMSO)

Figure 14A:
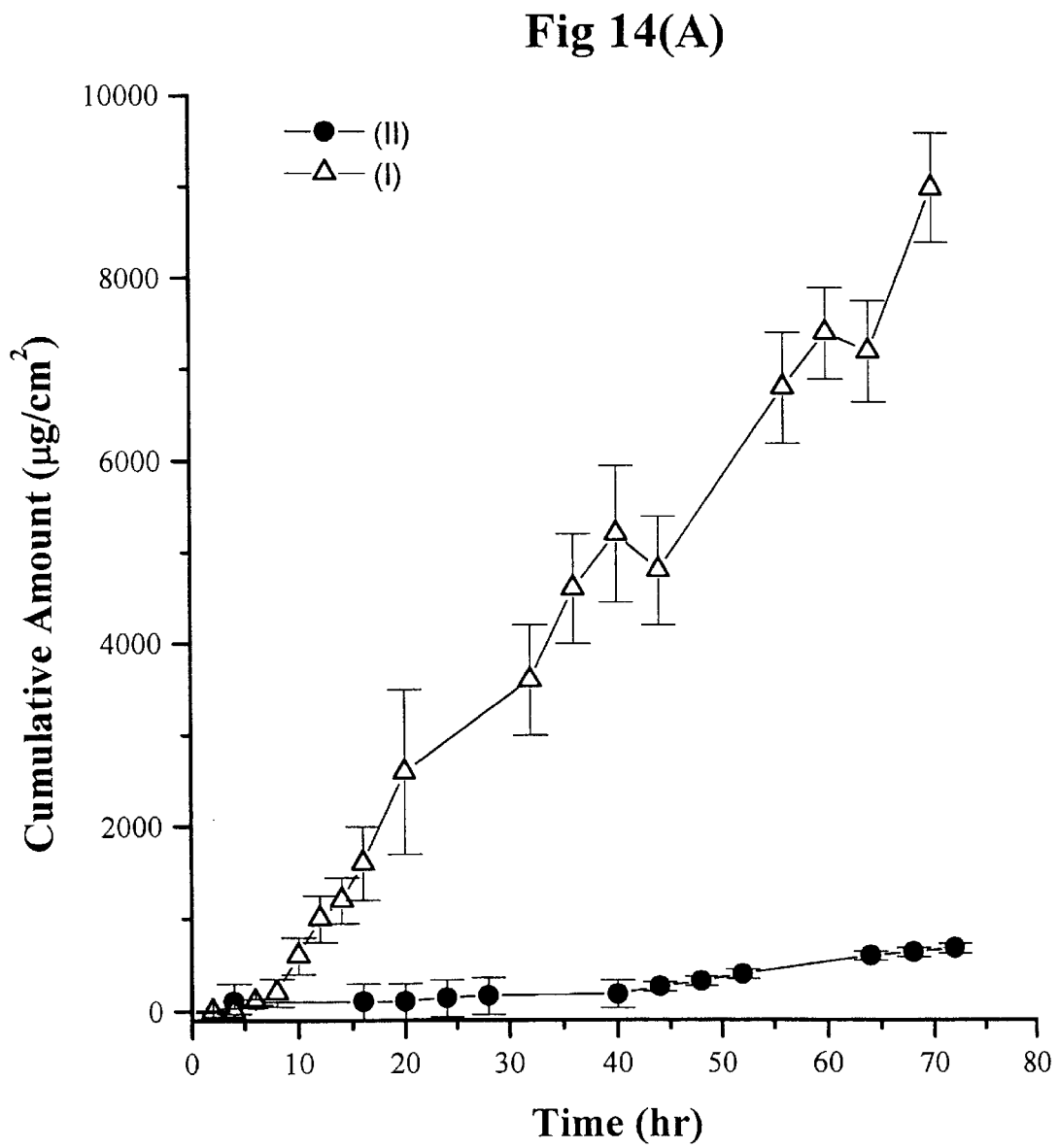
Figure 14B:
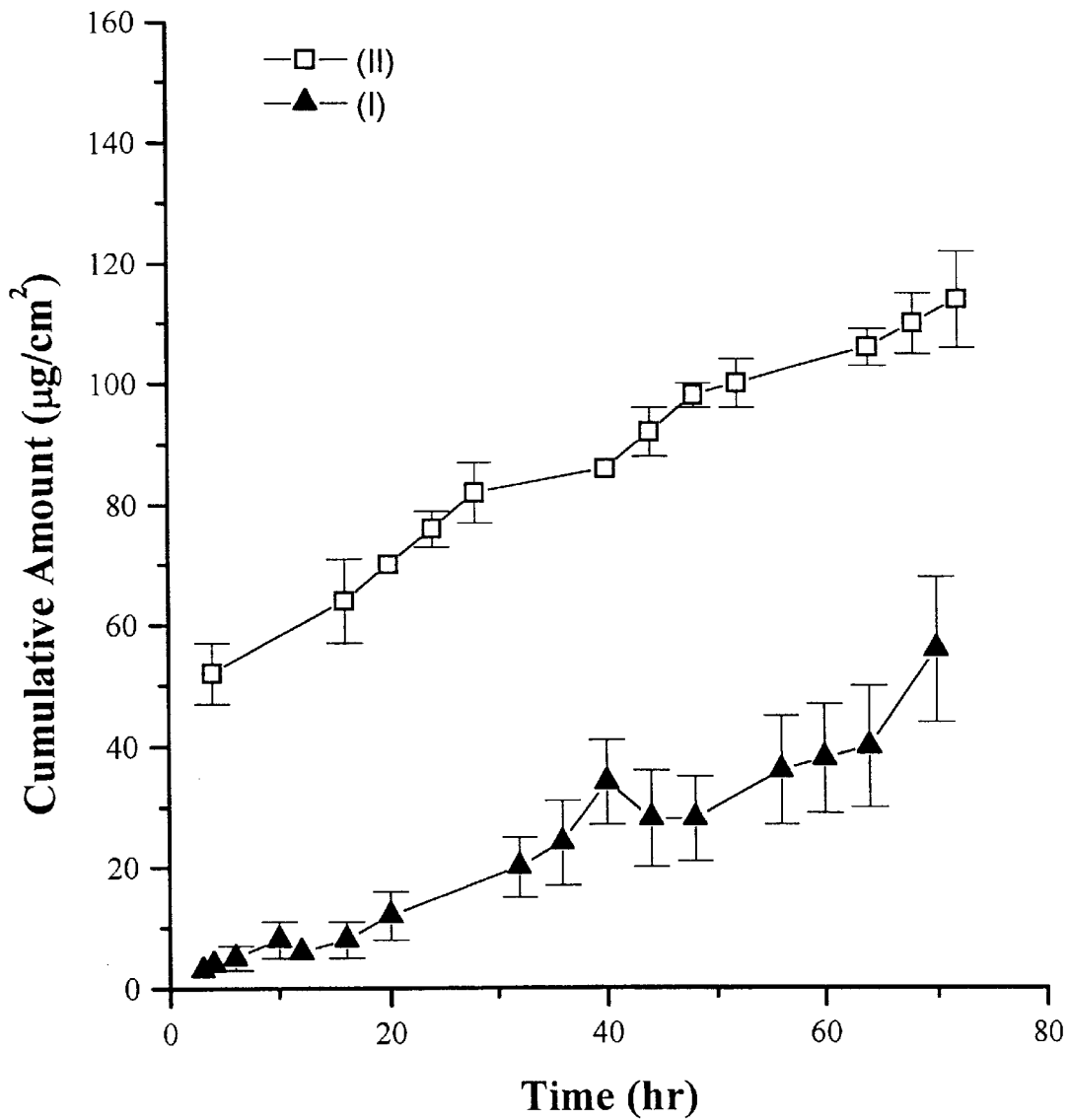

FIG. 14(A). G16 containing 20% terpineol
(I) rabbit abdominal skin
(II) human leg skin FIG. 14(B). G1 control
(I) human leg skin
(II) rabbit abdominal skin FIG. 15. Comparisons of auto-UV and traditional apparatus for transdermal penetration G1 . . . control (traditional apparatus)
G16 . . . 20% terpineol (traditional apparatus)
G1 . . . control (auto-UV apparatus)
G16 . . . 20% terpineol (auto-UV apparatus)

Figure 16A:
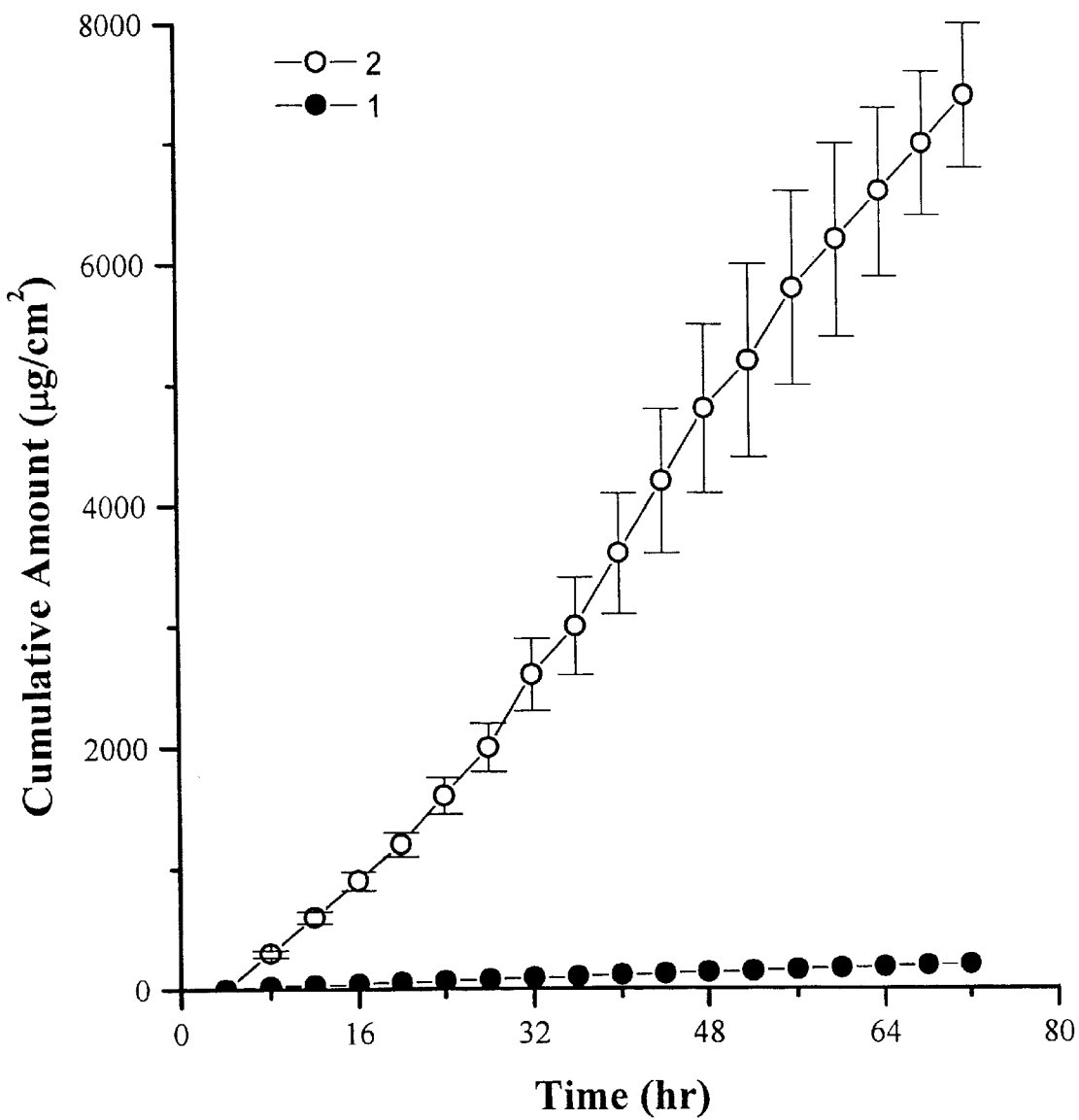
Figure 16B:
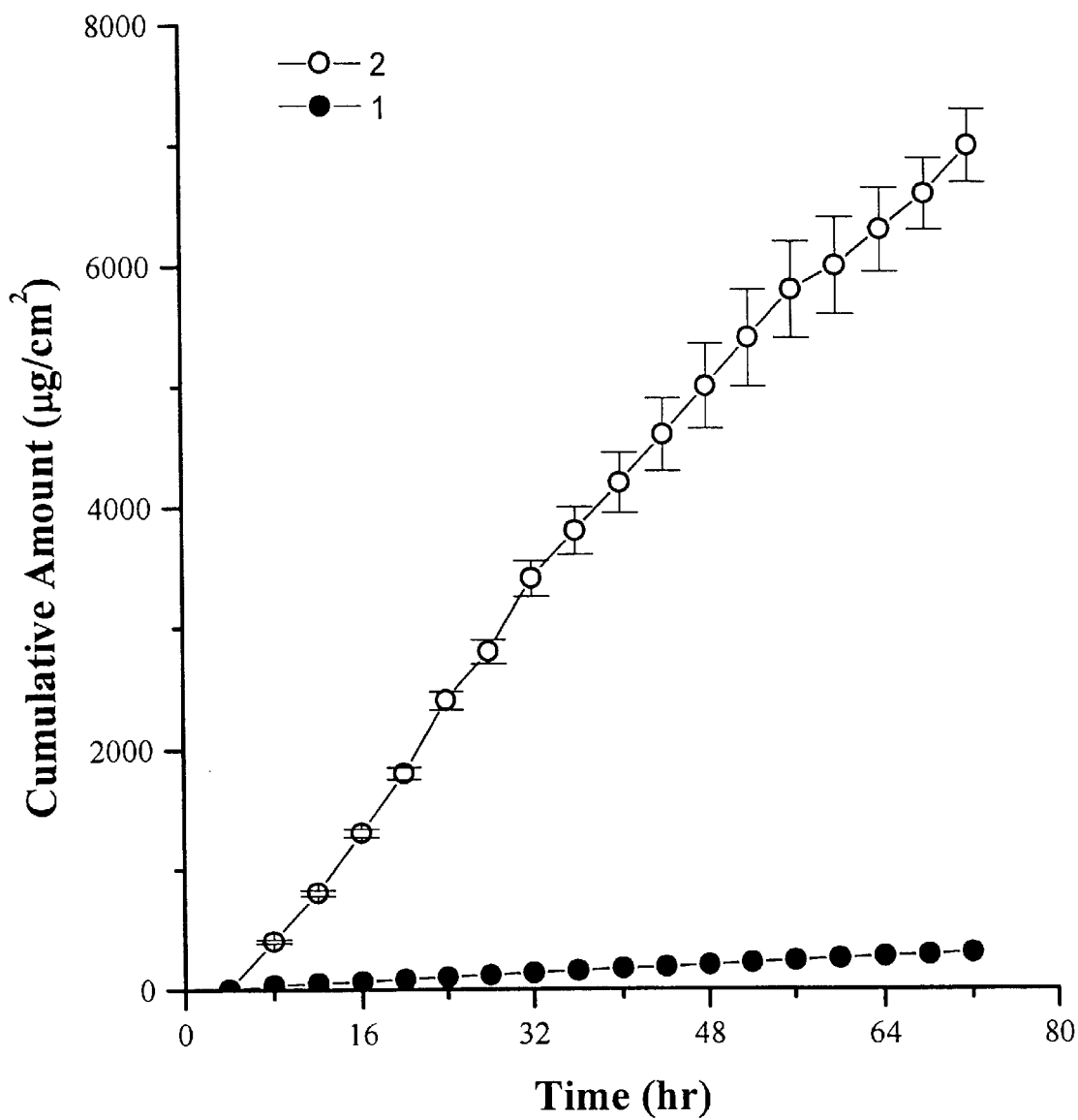
Figure 17A:
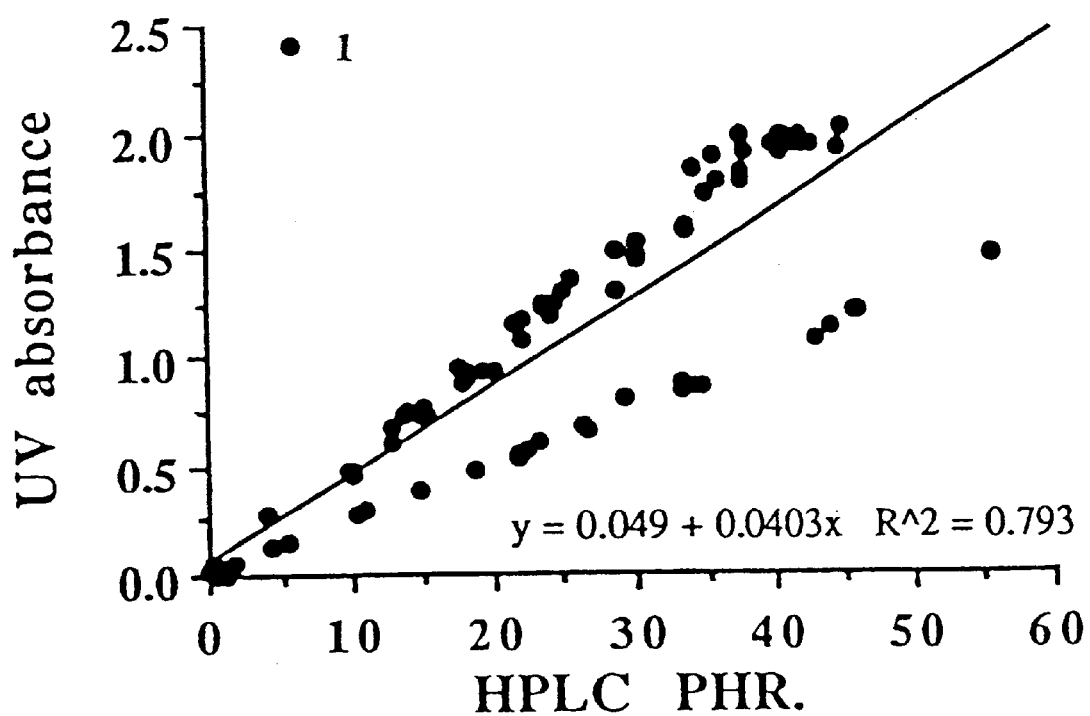
Figure 17B:
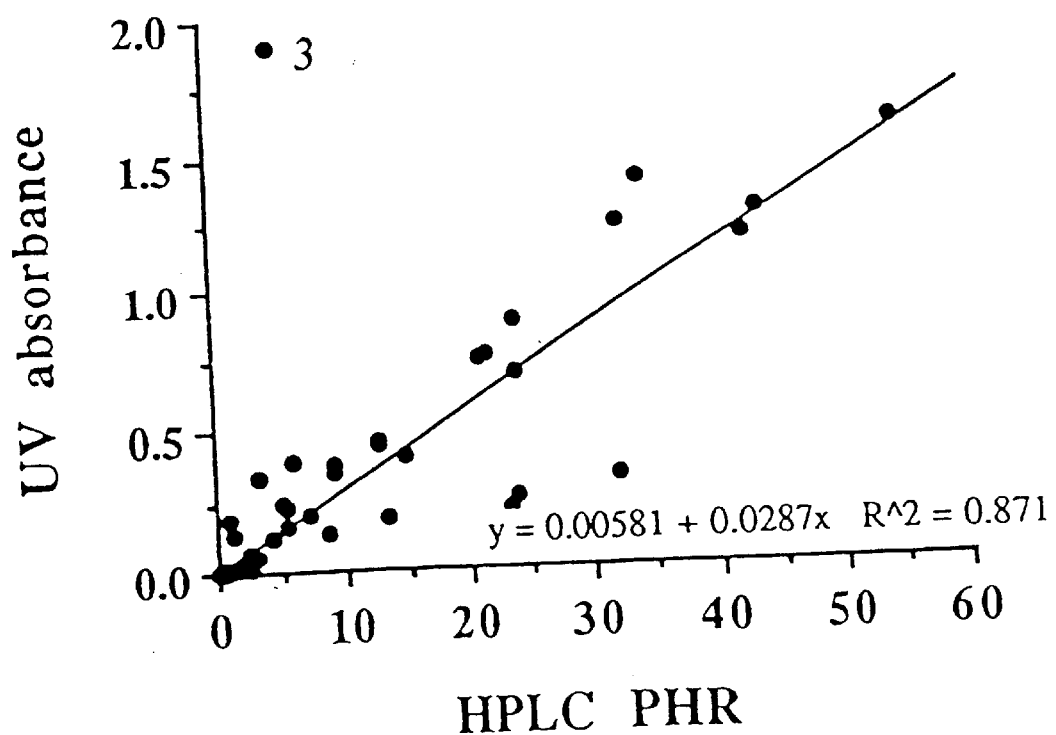

FIGS. 16(A)–16(B). Skin penetration of various anti-inflammatory agents on rabbit abdominal skin 16(A)
1. tenoxicam
2. tenoxicam+20% terpineol 16(B)
1. isoxicam+20% terpineol
2. isoxicam FIGS. 17(A)–17(B). Correlation between auto-UV and HPLC for oxicams 17(A) 1 . . . piroxicam
17(B) 2 . . . isoxicam
17(C) 3 . . . tenoxicam

DETAILED DESCRIPTION OF THE INVENTION

Figure 2:
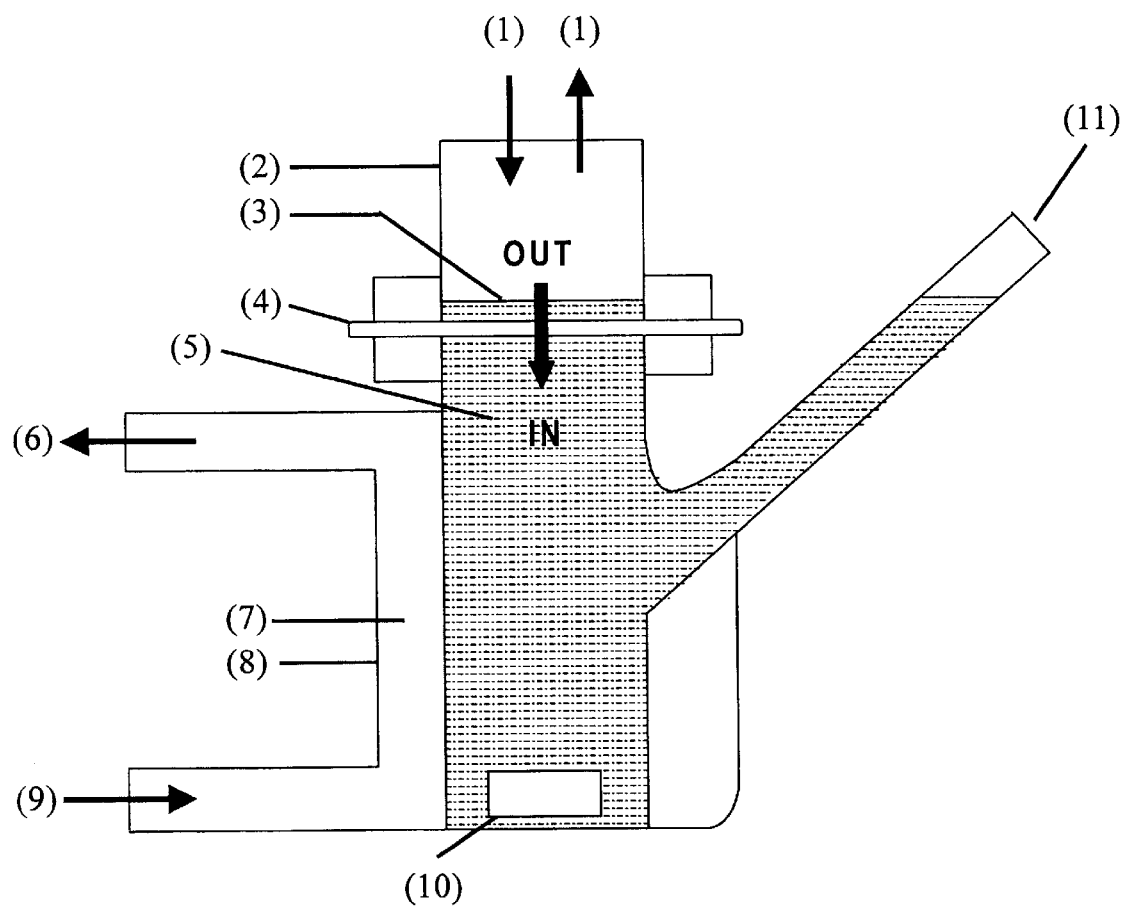
FIG. 2. In vitro transdermal penetration study apparatus
(1) air
(2) sample
(3) penetration accepting area
(4) skin
(5) accepting chamber
(6) water outlet
(7) circulated water flow
(8) diffusion cell
(9) water inlet
(10) magnetic bar
(11) sampling port FIG. 3(A)–FIG. 3(C). Transdermal penetration on nude mice abdominal skin using Chinese herb enhancers FIG. 3(A)
G6 . . . 5% trans-cinnamaldehyde
G7 . . . 2% trans-cinnamic acid
G4 . . . 5% pinene
G5 . . . 2% oleanolic acid
G2 . . . 2% glycyrrhizin
G1 . . . control FIG. 3(B)
G17 . . . 10% limonene
G29 . . . 10% lauryl alcohol
G 8 . . . 10% β-myrcene
G 3 . . . 5% β-myrcene
G 9 . . . 2% betulin
G 1 . . . control FIG. 3(C)
G16 . . . 20% terpineol
G13 . . . 15% terpineol
G11 . . . 10% terpineol
G12 . . . 10% terpineol+10% β-myrcene
G10 . . . 15% β-myrcene
G1 . . . control FIGS. 4(A)–4(B). Effect of various amounts of the same enhancer on piroxicam penetration on nude mice skin FIG. 4(A)
G10 . . . 15% β-myrcene
G 8 . . . 10% β-myrcene
G3 . . . 5% β-myrcene
G1 . . . control FIG. 4(B)
G16 . . . 20% terpineol
G11 . . . 10% terpineol
G13 . . . 15% terpineol
G 1 . . . control FIG. 5. Single enhancer or combined enhancers tested on nude mice skin
G11 . . . 10% terpineol
G12 . . . 10% β-myrcene+10% terpineol
G 8 . . . 10% β-myrcene
G 1 . . . control FIGS. 6(A)–6(C). Pure Chinese herb enhancer on rabbit abdominal skin FIG. 6(A)
G 7 . . . 2% trans-cinnamic acid
G19 . . . 10% ergosterol
G15 . . . 10% terphenyl
G14 . . . 5% epicatechin
G 1 . . . control FIG. 6(B)
G28 . . . 10% Tween 80
G31 . . . 2% cineole
G21 . . . 2% digitonin
G30 . . . 10% cineole
G1 . . . control FIG. 6(C)
G11 . . . 10% terpineol
G26 . . . 10% ethyl myristate
G12 . . . 10% β-myrcene+10% terpineol
G18 . . . 10% β-myrcene+15% terpineol
G 8 . . . 10% β-myrcene
G27 . . . 10% β-myrcene+10% ethyl myristate
G1 . . . control FIG. 7. Various concentrations of the same pure Chinese herb enhancer tested on rabbit abdominal skin
G16 . . . 20% terpineol
G32 . . . 30% terpineol
G11 . . . 10% terpineol
G 1 . . . control FIG. 8. Various concentrations of piroxicam in gels tested on rabbit abdominal skin
G25 . . . 5% piroxicam
G23 . . . 2% piroxicam
G24 . . . 3% piroxicam
G22 . . . 1% piroxicam
G 1 . . . control FIG. 9. Formula containing 20% terpineol using a different receiver phase tested on rabbit abdominal skin
G1 . . . control (receiver phase was pH 7.4 phosphate buffer)
G16 . . . 20% terpineol(receiver phase was pH 7.4 phosphate buffer)
G1 . . . control(receiver phase was 30% DMSO)

Apparatus for the in vitro test included a manual and an auto-UV apparatus, as shown in FIG. 2. The testing unit included a vertical Franz cell. The structure was a set of two vertical glass cells. These two cells could be separated. For testing, the lower cell was filled with 0.2 M phosphate buffer, and a stirring bar was placed at the bottom spinning at 600 rpm. Water was circulated in the interlayer to maintain a constant temperature. The top cell was filled with 0.5 ml or 0.5 g of different samples, and covered with a plastic film. Animal skin for testing was placed between two cells. Rabbit abdominal skin, nude mice abdominal skin, and human leg skin were used as a diffusion barrier. The lower and upper cells were fixed by metal clamps. Samples(200 $\mu$L) were drawn at fixed intervals via a sampling port. Upon sampling, the same volume of phosphate buffer was added to maintain a constant volume. The sample was added with 100 $\mu$L of isoxicam(30 $\mu$g/mL) for further HPLC analysis. The released amount was calculated according to the standard curve.

The auto apparatus was referred to the auto-UV system, which combined the traditional transdermal cells plus an UV flow cell. The traditional transdermal cell was a set of vertical Teflon containers. The bottom was see-through glass. The bottom container was attached with a multichannel cassette pump that could drive 30% of DMSO phosphate buffer through the diffusion and UV flow cells. The UV absorbance was recorded by a computer. The entire unit was placed in a stainless water bath at 32° C. A sample(0.5 ml or 0.5 g) for the different dosage form was placed in the top cell, and the upper opening was covered with plastic film. Each experiment included a blank to determine the UV absorption background.

Analogs of piroxicam were also tested using pure Chinese herb enhancers as absorption enhancers. Pure Chinese herb enhancers included oleanolic acid, trans-cinnamic acid, glycyrrhizin, β-myrcene, trans-cinnamaldehyde, cineole, terpineol, betulin, epicatechin, lauryl alcohol, ergosterol, terphenyl, pinene, limonene, digitonin, ethyl myristate, ursolic acid, and Tween 80. Enhancer can be any one of these or combinations. For example, pinene exits in Eucalypti Folium, with two types, α and β. It can further be distinguished as (−)-α, (+)-α or (−)-β, or (+)-β. In the natural herb, it could contain many types of pinene. For instance, α- and β-pinene are found in Valerianae Radix, Amomi Cardamomi, Magnoliae Cortex. However, in Asari Herba and Piperis Fructus have β-pinene only, whereas Perillae Herba, Menthae Herba, Zingiberis Rhizoma have α-pinene only. Cinae Flos has only has (−)-α-pinene, but in Amomi Cardamomi Fructus has both (+)-α- and (+)-β-pinene, and in Foeniculi Fructus there is (+)-α-pinene. Trans-cinnamic acid can be found in benzoinum, and trans-cinnamaldehyde can be found in Cinnamoni Cortex. Cineole can be found in Zingiberis Rhizoma, Cardamomi Fructus, Amomi Cardamomi Fructus, Eucalypti Folium, Magnoliae Flos, and Zedoariae Rhizoma. Cineole can be further distinguished as 1,8-cineole and 1,4-cineole. 1,8-cineole is found in Amomi Cardamomi Fructus, Cardamomi Fructus, Eucalypti Folium, Magnoliae Flos, and Zedoariae Rhizoma. 1,4-Cineole can be found in Zedoariae Rhizoma. For glycyrrhizin, it is found in Glycyrrhizae Radix. Myrcene is found in Amomi Cardamomi Fructus and Lupuli Strobilus. β-form Myrcene exits in Zingiberis Rhizoma. Oleanolic acid can be found in Forsythiae Fructus, Corni Fructus, Caryophylli Flos, and Zizyphi Fructus. Terpineol can be found in Cinae Flos, Valerianae Radix, and Eucalypti Folium. Terpineol has α-form, β-form, and (+)-α-form. α-form can be found in Amomi Cardamomi Fructus and Valerianae Radix, while (+)-α-form can be found in Cardamomi Fructus. Limonene can be found in Magnoliae Flos, Cardamomi Fructus, Foeniculi Fructus, and Zanthoxyli Fructus. Limonene can be further distinguished as (+)-form, (−)-form, and d-form. (+)-form can be found in Myristicae Semen, Perillae Herba and Schizonepetae Herba, whereas (−)-limonene can be found in Menthae Herba, and d-limonene in Citri Exocarpium. The structure of Epicatechin can be further distinguished as (+)-form and (−)-form. (−)-Epicatechin can be found in Cinnamoni Cortex et Caulis, Rhei Rhizoma, and Arecae Semen, while (+)-epicatechin can be found in Gambir. Betulin can be found in Platycodi Radix, and ergosterol can be found in Hoelen, Polyporus, Ergota, and Bufonis Venenum. Digitonin can be found in Digitalis Folium.

Figure 3C:
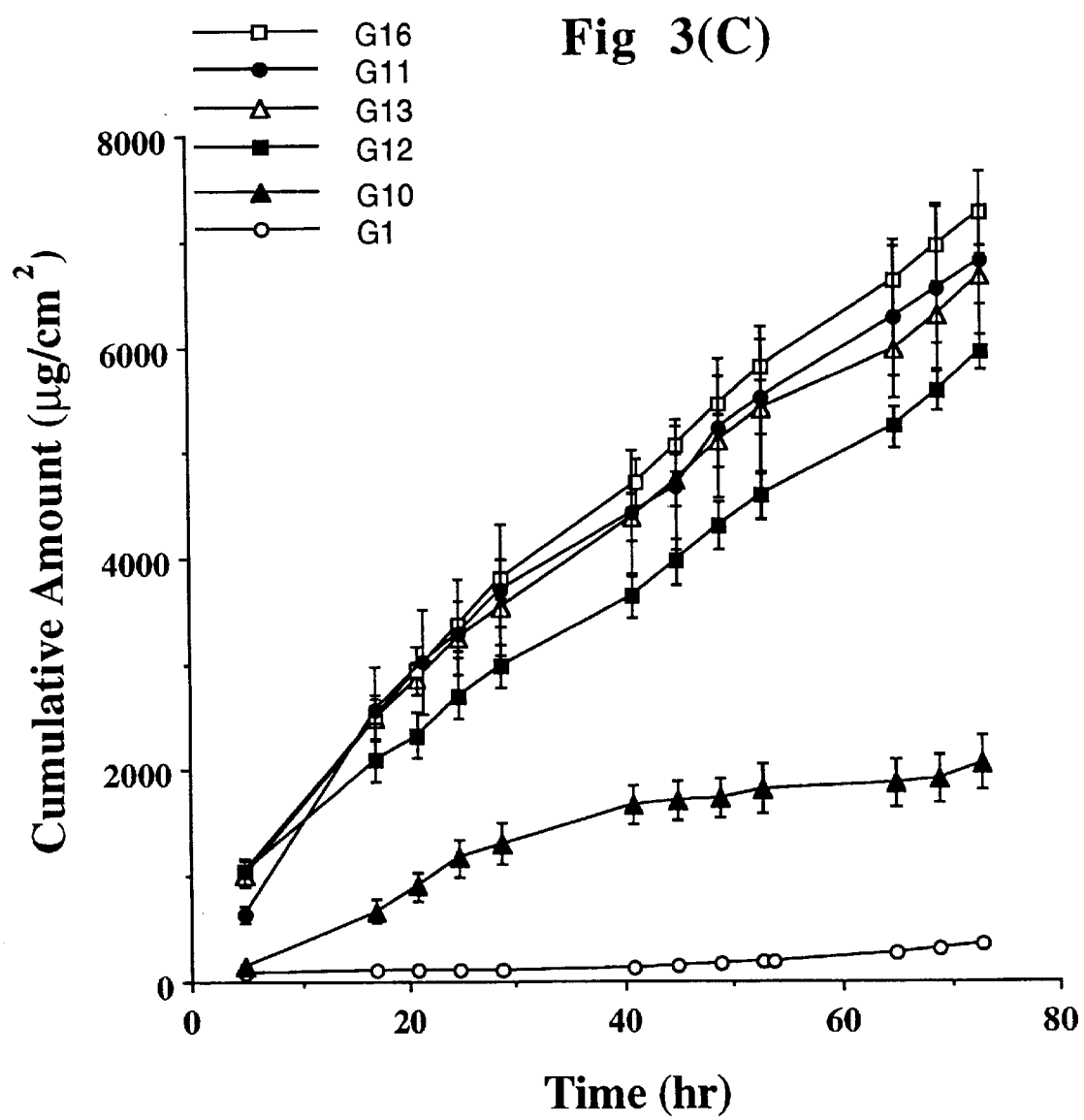

The present invention employed sodium carboxymethylcelluose (CMC) and ethylene glycol as a base, with the addition of various pure Chinese Herb enhancers as absorption enhancers in 4% piroxicam gel. In vitro penetration study was conducted in abdominal skin of nude mice. Accumulated amounts of penetration per unit area in 72 hours were reported in Table 3. Results were compared to the control. As shown in FIG. 3, formulation with terpineol produced the best result of penetration. Accumulated amounts of penetration of formulation G16 (20% terpineol) was 27.6 times the control. G11 containing 10% terpineol, was 25.9 times the control. G13 containing 15% of terpineol, was 25.4 times the control. G12 containing 10% β-myrcene with the same amount of terpineol of G12 was 22.6 times the control. Accumulated amount of penetration per unit area in 72 hrs of the control(G1) was 259.3 $\mu g/cm^2$, and others were as follows: G16 was 7,160.1 $\mu g/cm^2$, G11 6,716.2 $\mu g/cm^2$, G13 6,574.2 $\mu g/cm^2$, and G12 5,846.9 $\mu g/cm^2$.

Results of penetration for piroxicam gels containing the same herb enhancer with different concentrations are shown in FIG. 4. The amount penetrated per unit area for G10 containing 15% β-myrcene was 1,977.5 $\mu g/cm^2$, which was 7.6 times the control(G1, 259.3 $\mu g/cm^2$). And G16 containing 20% terpineol was 27.6 times the control. As shown in FIG. 5, G11 containing 10% terpineol only produced a better penetration than when combined with other enhancer when tested in the abdominal skin of nude mice.

Results of penetration in rabbit abdominal skin are shown in Table 4 and FIG. 6. The average accumulated amount of penetration per unit area in 72 hours of G16 containing 20% of terpineol was 157.6 times the control, and G32 containing 30% of terpineol was 149.7 times the control. G11 containing 10% of terpineol was 128 times the control. G18 containing 10% of terpineol mixed with 15% of β-myrcene was 116.9 times the control. G12 containing 10% of terpineol and the same amount of β-myrcene was 77.5 times the control. The average accumulated amount of penetration per unit area in 72 hrs for the control was 48.2 $\mu g/cm^2$, G16 was 7591.6 $\mu g/cm^2$, G32 was 7211 $\mu g/cm^2$, G11 was 6165.2 $\mu g/cm^2$, G18 was 5631 $\mu g/cm^2$, and G12 was 3730.8 $\mu g/cm^2$.

Effects of various enhancer concentrations on piroxicam gels are shown in FIG. 7. The average accumulated amount of penetration per unit area in 72 hrs of G16 containing 20% terpineol was 153.6 times the control. G32 containing 30% of terpineol was 149.7 times the control. Results of G11 containing 10% terpineol tested on rabbit abdominal skin are shown in FIG. 6C. This produced a better effect when combined with than other enhancers such as G12 and G18 formulae.

Effects of various amounts of piroxicam in the gel are reported in Table 5 and FIG. 8. Results showed that G25 containing 5% piroxicam had a penetration amount of 96.1 $\mu g/cm^2$, which was 2 times the control, 45.2 $\mu g/cm^2$. G23 containing 2% piroxicam had a penetration amount of 61.8 $\mu g/cm^2$, which was 1.6 times the control.

Figure 9:
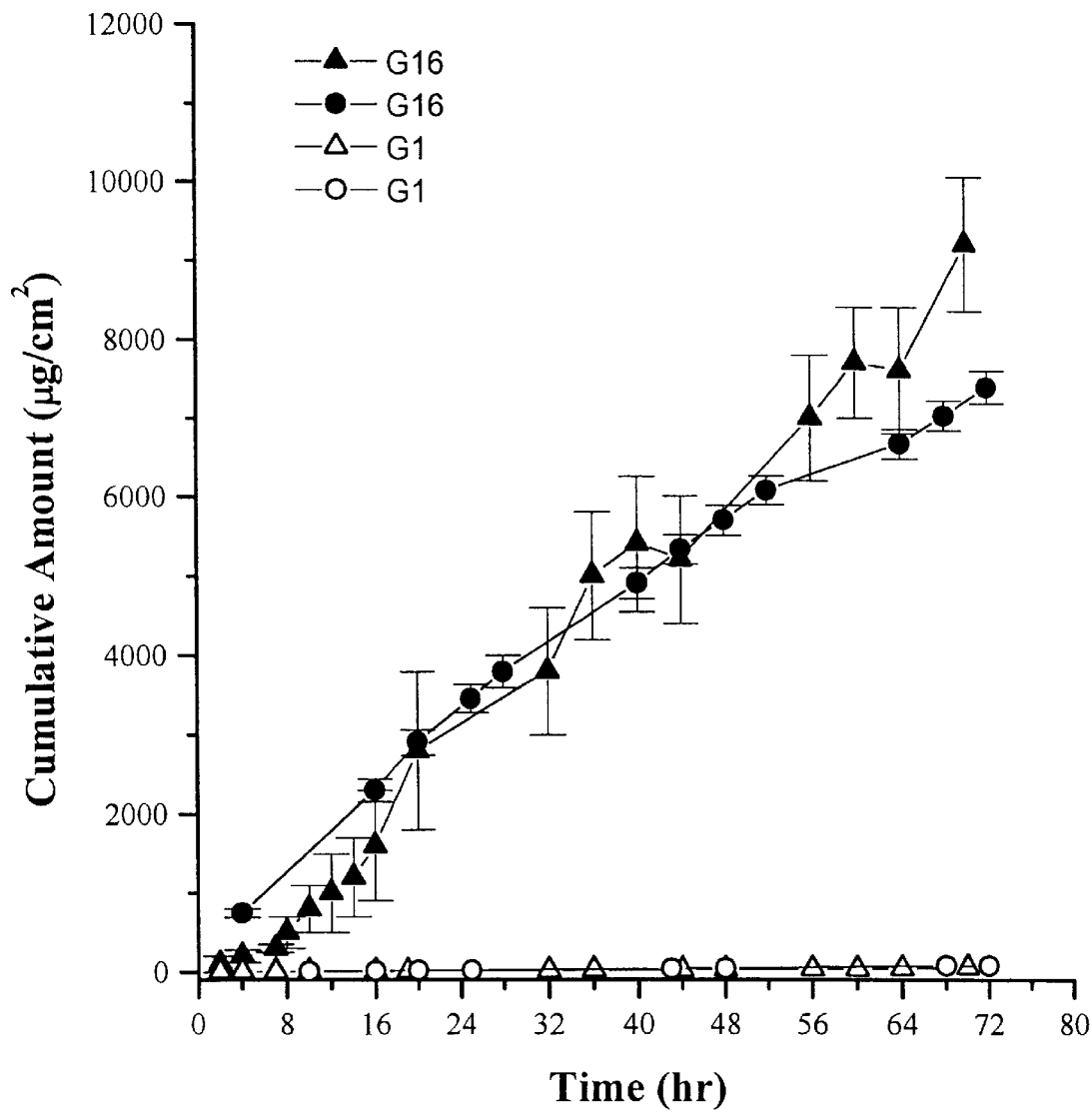

To test the effect of DMSO on the piroxicam penetration of rabbit abdominal skin, G16 containing 20% terpineol was tested using pH 7.4 phosphate buffer or mixed with 30% DMSO as the receiver phase. Results are shown in FIG. 9. Results showed that DMSO did not have any effect on penetration.

Figure 11:
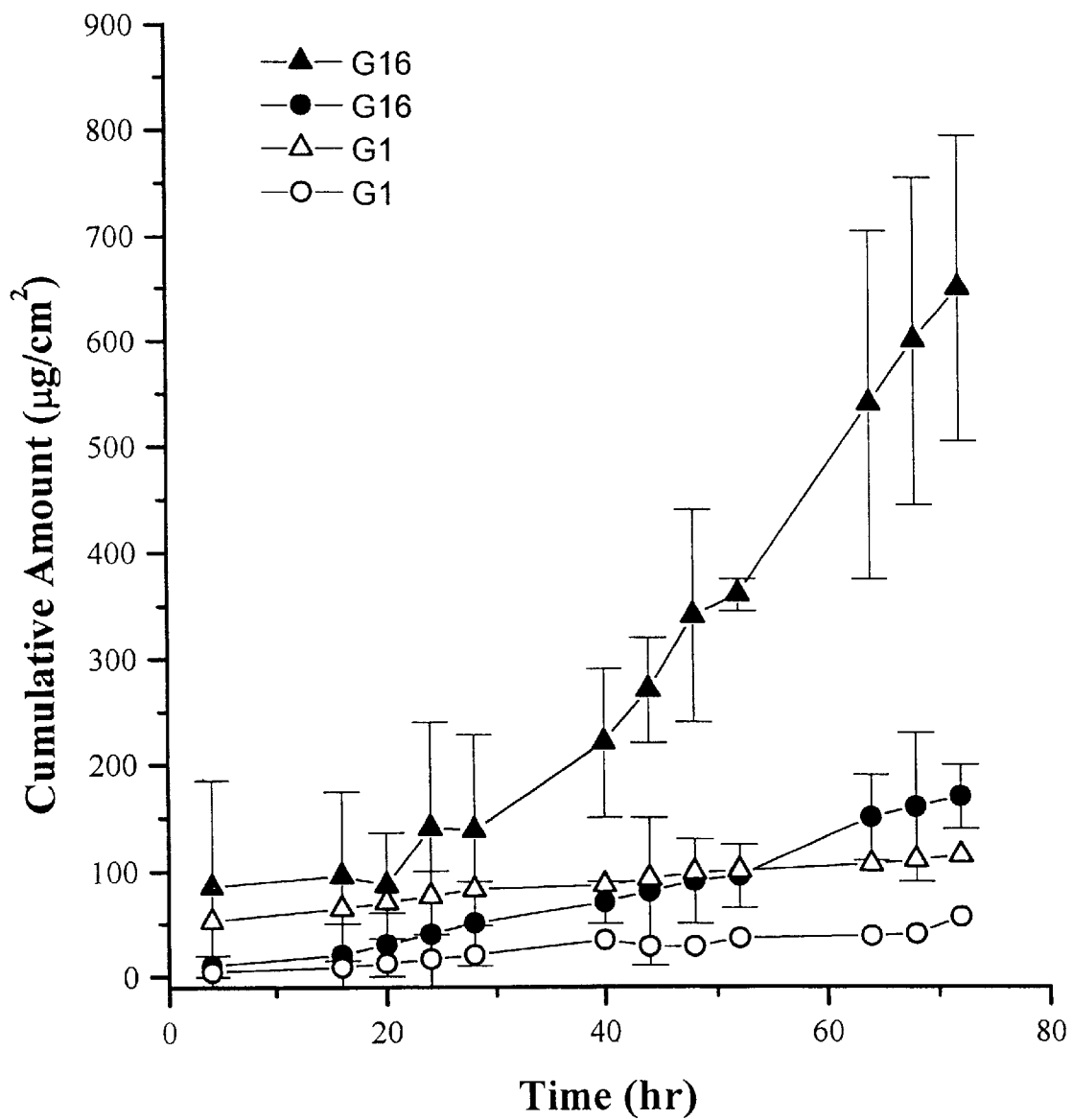

Results of piroxicam penetration on human leg skin are shown in Table 6 and FIG. 10. G16 containing 20% terpineol had the best results. The cumulated amount of penetration was 161.4 $\mu g/cm^2$, which was 18.4 times the control, 8.8 $\mu g/cm^2$. G12 was 110.2 $\mu g/cm^2$, which was 12.5 times the control. G8 was 55.1 $\mu g/cm^2$, which was 6.3 times the control. G16 containing only 20% terpineol was better than G12 containing multiple enhancers. As shown in FIG. 11, with or without 30% DMSO in the receiver phase did not have any effect on the penetration study on human leg skin. When G16 containing 20% terpineol was added with 20% of DMSO, the piroxicam penetration was worse than when using 20% terpineol alone.

Gels included G8 containing 10% myrcene, G12 containing 10% myrcene and 10% terpineol, G16 containing 20% terpineol, as well as the control G1 were tested on abdominal skin of nude mice(I), rabbit abdominal skin(II), and human leg skin(III) for the piroxicam penetration study in vitro. Results are shown in FIG. 13 and Table 7(A). In 72 hours, the accumulated amount of penetration per unit area for G1, G8, G12, and G16 on abdominal skin of nude mice was 29.5 times, 15.9 times, 53 times, and 44.4 times respective of that of human leg skin. In rabbit skin, the accumulated amounts of penetration per unit area for G1, G8, G12, and G16 were 5.5 times, 6.2 times, 33.8 times, and 47 times that of human leg skin. Results revealed that penetration on nude mice abdominal skin was 16 to 53 times that of human leg skin, while on rabbit abdominal skin it was 5 to 47 times that of human leg skin. In addition, G16 containing 20% terpineol using 30% DMSO in phosphate butter as a receiver phase on rabbit abdominal skin produced a 14 times higher penetration amount than on human leg skin, while the control was 0.5 times.

Figure 15:
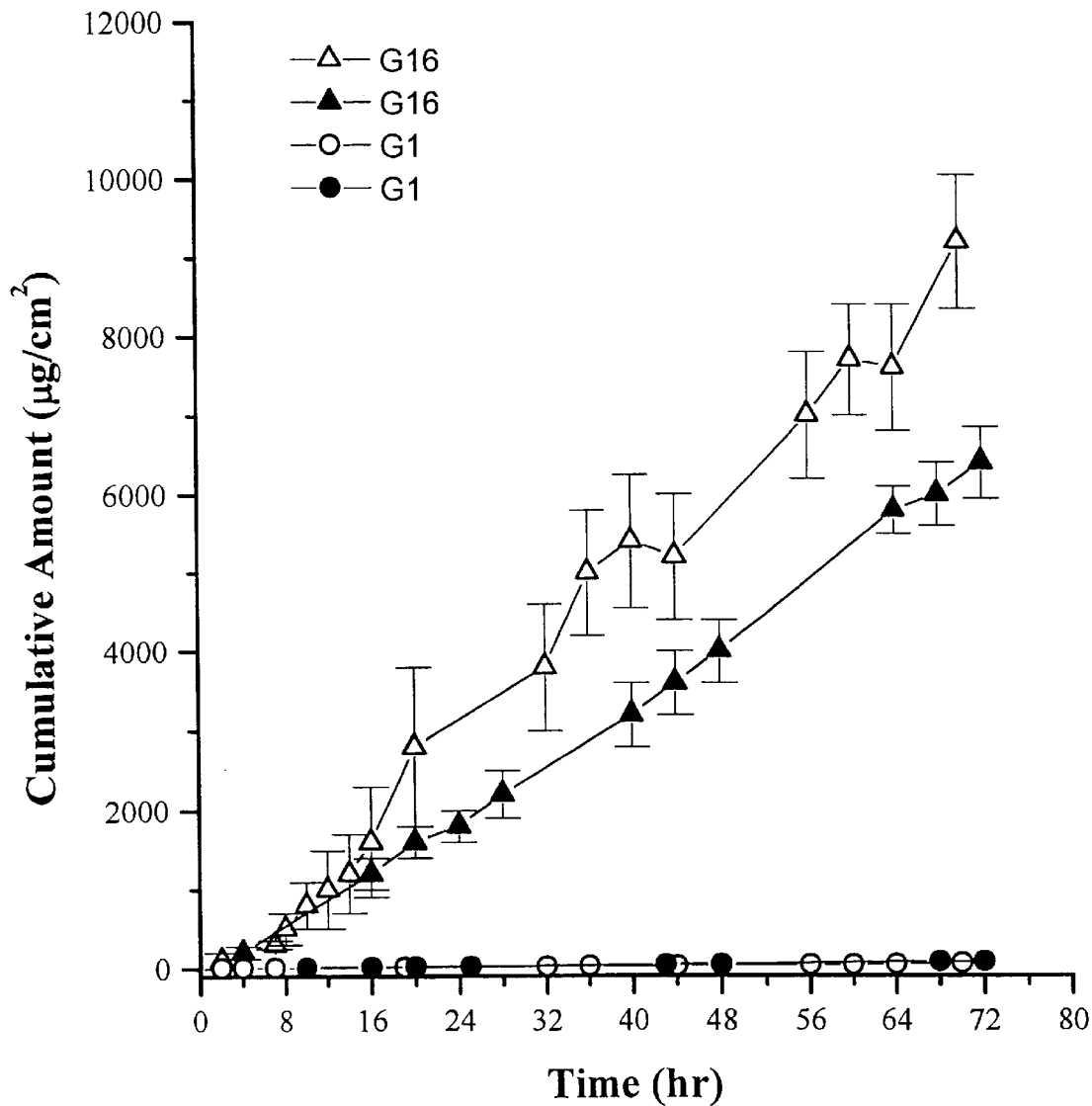
Figure 17C:
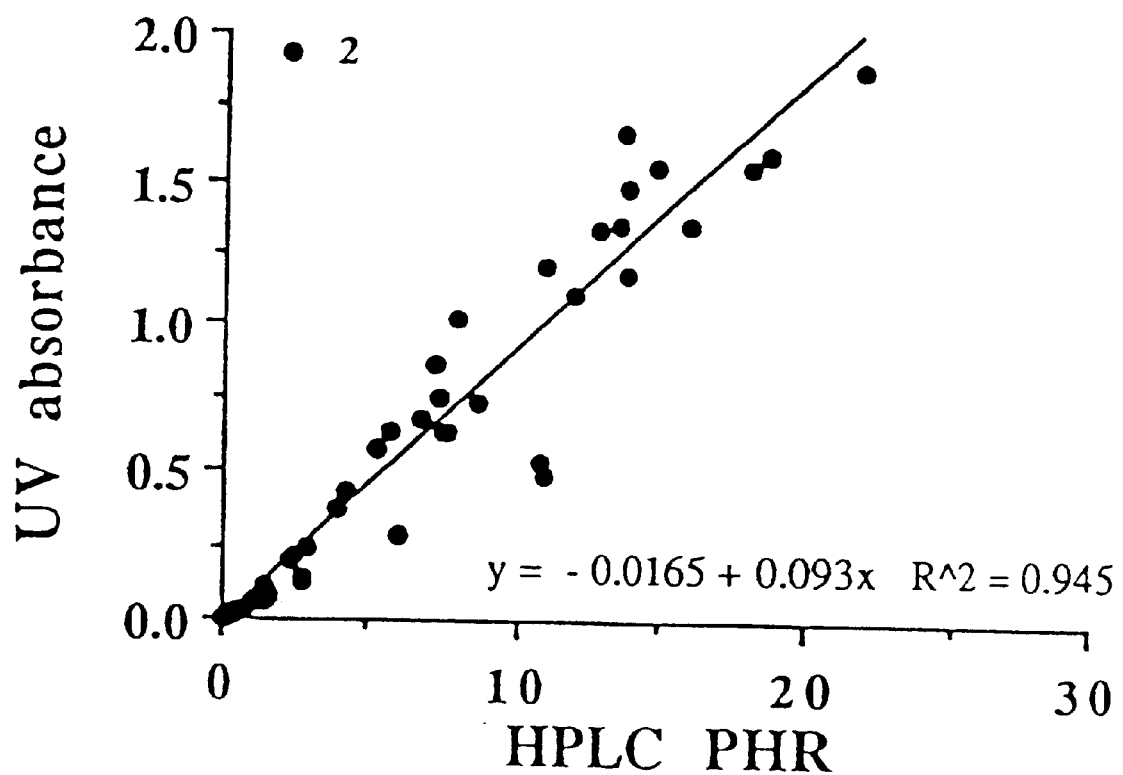

A comparison of piroxicam penetration and accumulated amounts of piroxicam G1 and G16 between manual and auto-UV units is reported in FIG. 15. In 72 hours, the average accumulated amount of piroxicam penetration per unit area for G1 and G16 in the auto-UV system was 90.5 $\mu g/cm^2$ and 72 $\mu g/cm^2$, respectively. Results showed that the auto-UV system was not significantly different from a traditional system when tested with G1(the control), although G16 showed some variation. FIG. 17 showed the linear correlation between auto-UV and HPLC assay.

The penetration of tenoxicam and isoxicam in the base containing sodium carboxymethylcellulose, ethylene glycol and with or without 20% terpineol using 30% DMSO buffer in the receiver phase was studied on rabbit abdominal skin. Results showed that the accumulated amount of penetration in 72 hours of the control was 372.8 $\mu g/cm^2$ for isoxicam. For tenoxicam with 20% terpineol the cumulated penetration amount was 7276.5 $\mu g/cm^2$, which was 86.3 times the control. Isoxicam was 6928.9 $\mu g/cm^2$, which was 18.6 times the control. This result shows that the present invention was also applicable to other oxicam anti-inflammatory agents.

Excipients used in the present invention included polyethylene glycol, sodium carboxymethylcellulose, glycerin, and ethylene glycol. Transdermal preparations in the present invention included preparations, such as ointments, suspensions, gels, solutions, aerosols, local paste and patches which were intended for absorption via the skin and mucous membranes.

The present invention is related to a transdermal preparation of oxicams. This invention employed a high purity of Chinese herbal enhancers as transdermal absorption enhancers. The transdermal preparation included an active ingredient possessing anti-inflammatory, pyretic, and analgesic properties, ranging from 0.1% to 50%. In the preparation, a transdermal absorption enhancer, ranging from 0.1% to 70% of a pure Chinese herb enhancer was used. Other necessary excipients for transdermal preparation were also employed. The amount of necessary excipient ranged from 0.01% to 99.95%, which was a mixture of sodium carboxymethylcellulose and ethylene glycol. Pharmaceutical preparations that may utilize the present invention include ointments, suspensions, gels, solutions, emulsions, lotions, pastes, patches, aerosols, and other preparations intended for local use. The active ingredient was referred to anti-inflammatory agents whose structures were oxicams. Their structures are shown in FIG. 1, presenting as piroxicam, sudoxicam, tenoxicam, isoxicam, cinnoxicam, and lomoxicam. Better choices were piroxicam, isoxicam, and tenoxicam. In this invention, the transdermal preparation was comprised of 0.1% to 50% of an oxicam, 0.1% to 70% of pure Chinese herb enhancers as enhancers, as well as other necessary excipients for transdermal delivery of the active ingredients. Based on results from testing this preparation on nude mice skin, rabbit leg skin, and human leg skin, it was found that skin penetration of piroxicam of the transdermal preparation containing 20% terpineol oil was 157.6 times higher than that of the control group.

EXAMPLES

The present invention will be more clearly understood with reference to the following examples.

Example 1 Preparation of piroxicam gel

Piroxicam 4% (w/w) was dissolved in ethylene glycol 20% (w/w). Sodium carboxymethylcellulose 2% (w/w) was dissolved in water. Then two solutions were mixed well in a mortar, and adjusted to 100 ml with water.

Example 2 Preparation of piroxicam gel containing 2% glycyrrhizin

4% (w/w) piroxicam and 2% (w/w) glycyrrhizin were weighed precisely then dissolved in 20% (w/w) ethylene glycol. Then 2% (w/w) of sodium carboxymethylcellulose was dissolved in water. The two solutions were mixed well in a mortar, followed by the addition of water to 100 ml.

Example 3 to 7 Preparation of piroxicam gels containing 20% various pure Chinese herb enhancers Same as the preparation method in example 2, 2% (w/w) oleanolic acid, betulin, ursoic acid, digitonin, or trans-cinnamic acid was weighed precisely and separately added to the formula of piroxicam gels.

Example 8 to 11 Preparation of piroxicam gels containing 5% various pure Chinese herb enhancers Same as the preparation method in example 2, 5% (w/w) trans-cinnamaldehyde, (+)-catechin, (1s)-(–)-α-pinene, or β-myrcene was separately added to the formula of piroxicam gels.

Example 12 to 20 Preparation of piroxicam gels containing 10% various pure Chinese herb enhancers Same as the preparation method in example 2, 10% (w/w) β-myrcene, terpineol, ethyl myristate, ergosterol, ((+)-limonene), terphenyl, lauryl alcohol, or cineole was separately added to the formula of piroxicam gels. 10% Tween 80 was also used to prepare piroxicam gels.

Example 21 to 25 Preparation of piroxicam gels containing 15%, 20%, or 30% various pure Chinese herbal enhancers Same as the preparation method in example 2, 15% (w/w) β-myrcene, or terpineol, 20% (w/w) terpineol, or cineole, or 30% (w/w) terpineol was separately added to prepare piroxicam gels.

Example 26 to 28 Preparation of piroxicam gels containing two pure Chinese herbal composition enhancers Same as the preparation of example 3, 10% (w/w) β-myrcene and 10% (w/w) terpineol were added; or 10% (w/w) ethyl myristate and 10% (w/w) terpineol were added; or 15% (w/w) β-myrcene mixed with 10% (w/w) terpineol were added to the formula to prepare various piroxicam gels containing two enhancers.

Example 29 Preparation of tenoxicam gel

4% (w/w) tenoxicam was weighed and dissolved in 20% (w/w) ethylene glycol. 2% (w/w) sodium carboxymethylcellulose was dissolved in water. These two solutions were then mixed well in a mortar, and adjusted to 100 ml with water.

Example 30 Preparation of isoxicam gel

4% (w/w) isoxicam was precisely weighed and dissolved in 20% (w/w) ethylene glycol. 2% (w/w) sodium carboxymethylcellulose(CMC) was dissolved in water. Then the two solutions were mixed well in a mortar, followed by the adding of an appropriate amount of water to 100 ml.

Example 31 Preparation of isoxicam gel containing 20% terpineol

4% (w/w) isoxicam and 20% (w/w) terpineol were precisely weighed and dissolved in 20% (w/w) ethylene glycol. 2% (w/w) sodium carboxymethylcellulose(CMC) was dissolved in water. The two solutions were then mixed well in a mortar, followed by the addition of an appropriate amount of water to 100 ml.

Example 32 Preparation of tenoxicam gel containing 20% terpineol

4% (w/w) isoxicam and 20% (w/w) terpineol were precisely weighed and dissolved in 20% (w/w) ethylene glycol. 2% (w/w) sodium carboxymethylcellulose was dissolved in water. Then the two solutions were mixed well in a mortar, followed by the addition of an appropriate amount of water to 100 ml.

Example 33 Procedure of sampling and analysis

Skins of human leg skin, or rabbit abdominal skin, or the abdominal skin of 7 to 9 week old female ICR nude mice were placed in the interface of diffusion cells and fixed by metal clamps. Each experiment was performed for 72 hours. At a preset interval, 200 $\mu$L of samples were removed from the sampling port. Upon withdrawing, the same amount of 0.05 M phosphate buffer was added to maintain the same volume. Samples were analyzed by HPLC. The exact amount of penetration was calculated according to the standard curve.

TABLE 1

| Name | Source | Catalog | M.I. No. |
|---|---|---|---|
| glycyrrhizin | Glycyrrhizae Radix | Triterpenoid saponin | 4401 |
| cineole | Zedoariae Rhizoma, Amomi Cardamomi Fructus, Eucalyti Folis, Cardamomi Fructus, | Essential oil-oxide | 3402 |
| myrcene | Amomi Cardamomi Fructus, Hupulis Strobilus, Zingiberis Rhizoma | Essential oil | 6243 |
| pinene | Valeriae Radix, Amomi Cardamomi, Asari Herba, Magnoliae Cortex, Foeniculi Fructus, Piperis Fructus, Perillae Herba, Menthae Herba, Zingiberis Rhizoma, Cinae Flos, Amomi Cardamomi Fructus | Essential oil | 7414 |
| trans-cinnamic acid | benzoin, | | 2300 |
| trans-cinnaldehyde | Cinnamoni Cortex | Essential oil-aldehyde | 2298 |
| oleanolic acid | Forsythiae Fructus, Corni Fructus, Caryophylli Flos, Ziziphyi Fructus. | Triterpenoid | 6787 |
| terpineol | Cinae Flos, Valeriae Radix, Eucalyti Folium, Valeriae Radix, Amomi Cardamomi Fructus, Cardamomi Fructus. | | 9103 |
| limonene | Magnoliae Flos, Cardamomi Fructus, Foeniculi Fructus, Zanthoxyli Fructus, Myristae Semen, Citri Exocarpium, Menthae Herba, Perillae Herba Schizonepetae Herba,. | | 5371 |
| epicatechin | Cinnamoni Cortex et Caulis, Gambir, Rhei Rhizoma, Arecae Semen, | Flavonoid | |
| betulin | Platycodi Radix, | Triterpenoid | 1212 |
| ergosterol | Hoelen, Polyporus, Ergota, bufonis Venenum | Sterol | 3607 |
| digitonin | Digitalis Folium | Cardiac glycoside | 3144 |

TABLE 2(A)

| | Constituents | | | | | | | | | | | | | | | | | | |
|---|---|---|---|---|---|---|---|---|---|---|---|---|---|---|---|---|---|---|---|
| | G1 | G2 | G3 | G4 | G5 | G6 | G7 | G8 | G9 | G10 | G11 | G12 | G13 | G14 | G15 | G16 | G17 | G18 | G19 |
| Piroxicam | 4 | 4 | 4 | 4 | 4 | 4 | 4 | 4 | 4 | 4 | 4 | 4 | 4 | 4 | 4 | 4 | 4 | 4 | 4 |
| Sodium CMC | 2 | 2 | 2 | 2 | 2 | 2 | 2 | 2 | 2 | 2 | 2 | 2 | 2 | 2 | 2 | 2 | 2 | 2 | 2 |
| Ethylene Glycol | 20 | 20 | 20 | 20 | 20 | 20 | 20 | 20 | 20 | 20 | 20 | 20 | 20 | 20 | 20 | 20 | 20 | 20 | 20 |
| Glycyrrhizin | | 2 | | | | | | | | | | | | | | | | | |
| Cineole | | | | | | | | | | | | | | | | | | | |
| β-Myrcene | | | 5 | | | | 10 | | 15 | | 10 | | | | | | | 15 | |
| (1s)-(-)-α-Pinene | | | | 5 | | | | | | | | | | | | | | | |
| Oleanolic acid | | | | | 2 | | | | | | | | | | | | | | |
| Ursolic acid | | | | | | | | | | | | | | | | | | | |
| trans-Cinnamaldehyde | | | | | | 5 | | | | | | | | | | | | | |
| trans-Cinnamic acid | | | | | | | 2 | | | | | | | | | | | | |
| α-Terpineol | | | | | | | | | | 10 | 10 | 15 | | | | 20 | | 10 | |
| Betulin | | | | | | | | 2 | | | | | | | | | | | |
| (+)-Limonene | | | | | | | | | | | | | | | | | 10 | | |
| Epicatechin | | | | | | | | | | | | | | 5 | | | | | |
| p-Terphenyl | | | | | | | | | | | | | | | 10 | | | | |
| Digitonin | | | | | | | | | | | | | | | | | | | |
| Ethyl myristate | | | | | | | | | | | | | | | | | | | |
| Ergosterol | | | | | | | | | | | | | | | | | | | 10 |
| Tween 80 | | | | | | | | | | | | | | | | | | | |
| Lauryl alcohol | | | | | | | | | | | | | | | | | | | |
| Water | 74 | 72 | 69 | 69 | 72 | 69 | 72 | 64 | 72 | 59 | 69 | 54 | 59 | 69 | 64 | 54 | 64 | 49 | 64 |

TABLE 2(B)

| | Constituents | | | | | | | | | | | | |
|---|---|---|---|---|---|---|---|---|---|---|---|---|---|
| | G20 | G21 | G22 | G23 | G24 | G25 | G26 | G27 | G28 | G29 | G30 | G31 | G32 |
| Piroxicam | 4 | 4 | 1 | 2 | 3 | 5 | 4 | 4 | 4 | 4 | 4 | 4 | 4 |
| Sodium CMC | 2 | 2 | 2 | 2 | 2 | 2 | 2 | 2 | 2 | 2 | 2 | 2 | 2 |
| Ethylene Glycol | 20 | 20 | 20 | 20 | 20 | 20 | 20 | 20 | 20 | 20 | 20 | 20 | 20 |
| Glycyrrhizin | | | | | | | | | | | | | |
| Cineole | | | | | | | | | | | 10 | 20 | |
| β-Myrcene | | | | | | | | | | | | | |
| (1s)-(−)-α-Pinene | | | | | | | | | | | | | |
| Oleanolic acid | | | | | | | | | | | | | |
| Ursolic acid | 2 | | | | | | | | | | | | |
| trans-Cinnamaldehyde | | | | | | | | | | | | | |
| trans-Cinnamic acid | | | | | | | | | | | | | |
| α-Terpineol | | | | | | | | 10 | | | | | 30 |
| Betulin | | | | | | | | | | | | | |
| (+)-Limonene | | | | | | | | | | | | | |
| Epicatechin | | | | | | | | | | | | | |
| p-Terphenyl | | | | | | | | | | | | | |
| Digitonin | | | 2 | | | | | | | | | | |
| Ethyl myristate | | | | | | | 10 | 10 | | | | | |
| Ergosterol | | | | | | | | | | | | | |
| Tween 80 | | | | | | | | | | 10 | | | |
| Lauryl alcohol | | | | | | | | | | | 10 | | |
| Water | 72 | 72 | 77 | 76 | 75 | 73 | 64 | 54 | 64 | 64 | 64 | 54 | 44 |

TABLE 3

| Formula | n = | 72 hr Mean | SE | Ratio | rank | Flux (μg/hr * cm²) | SD | Lag time (hr) | SD | $k_p$ (cm/hr) | SD | D (cm²/hr) | SD | P | SD |
|---|---|---|---|---|---|---|---|---|---|---|---|---|---|---|---|
| G1 | 52 | 259.34 | 15.31 | 1.00 | 11 | 1.18 | 0.57 | −1.71 | 0.65 | 2.95E−5 | 1.43E−5 | −6.1E−5 | 1.6E−4 | −0.01 | 0.00 |
| G2 | 6 | 144.94 | 25.49 | 0.56 | 15 | 2.96 | 1.43 | 20.39 | 10.05 | 7.40E−5 | 3.58E−5 | 6.0E−6 | 4.0E−6 | 0.47 | 0.53 |
| G3 | 5 | 451.69 | 94.16 | 1.74 | 9 | 10.01 | 4.25 | 28.36 | 3.82 | 2.50E−4 | 1.06E−4 | 3.0E−6 | 1.0E−6 | 1.75 | 0.50 |
| G4 | 6 | 258.07 | 46.67 | 1.00 | 12 | 3.26 | 1.45 | −10.59 | 12.31 | 8.15E−5 | 3.63E−5 | 2.7E−5 | 7.1E−5 | −0.12 | 0.18 |
| G5 | 6 | 255.27 | 28.56 | 0.98 | 14 | 7.04 | 1.66 | 35.90 | 2.84 | 1.76E−4 | 4.15E−5 | 3.0E−6 | 1.0E−6 | 1.62 | 0.38 |
| G6 | 5 | 255.55 | 51.44 | 0.99 | 13 | 4.67 | 1.71 | 20.11 | 5.51 | 1.17E−4 | 4.28E−5 | 6.0E−6 | 4.0E−6 | 0.55 | 0.19 |
| G7 | 6 | 68.28 | 10.41 | 0.26 | 16 | 1.05 | 0.51 | 5.83 | 9.94 | 2.63E−5 | 1.28E−5 | 2.1E−5 | 6.3E−5 | 0.04 | 0.06 |
| G8 | 5 | 873.60 | 78.02 | 3.37** | 7 | 13.28 | 1.23 | −27.24 | 8.57 | 3.32E−4 | 3.08E−5 | −3.8E−6 | 1.2E−5 | −2.17 | 0.06 |
| G9 | 5 | 311.38 | 75.56 | 1.20 | 10 | 11.20 | 7.53 | 41.75 | 7.11 | 2.80E−4 | 1.88E−4 | 3.0E−6 | 4.0E−6 | 4.72 | 3.95 |
| G10 | 6 | 1977.51 | 258.28 | 7.63*** | 5 | 7.63 | 0.45 | 190.63 | 10.45 | 1.91E−4 | 1.14E−5 | 5.5E−7 | 2.3E−4 | 8.72 | 0.00 |
| G11 | 5 | 6716.23 | 826.55 | 25.90*** | 2 | 73.52 | 17.83 | −19.50 | 7.67 | 1.84E−3 | 4.46E−4 | −1.3E−5 | 1.1E−5 | −7.89 | 6.25 |
| G12 | 6 | 5846.85 | 171.25 | 22.55*** | 4 | 70.72 | 2.35 | 563.63 | 0.36 | 1.77E−3 | 5.86E−5 | 1.8E−7 | 2.9E−4 | 239.16 | 0.01 |
| G13 | 6 | 6574.22 | 279.81 | 25.35*** | 3 | 25.35 | 0.27 | 633.75 | 0.27 | 6.34E−4 | 6.82E−6 | 2.1E+1 | 4.8E−1 | 2.41 | 0.00 |
| G16 | 5 | 7160.11 | 391.56 | 27.61*** | 1 | 77.97 | 14.91 | −21.08 | 8.41 | 1.95E−3 | 3.73E−4 | −6.6E−6 | 3.2E−6 | −9.14 | 3.82 |
| G17 | 6 | 1128.08 | 179.36 | 4.35*** | 6 | 20.60 | 6.75 | 18.44 | 6.35 | 5.15E−4 | 1.69E−4 | 7.5E−6 | 4.6E−6 | 2.18 | 0.96 |
| G29 | 6 | 610.09 | 58.94 | 2.35* | 8 | 13.78 | 3.97 | 26.86 | 8.12 | 3.45E−4 | 9.93E−5 | 4.3E−6 | 2.6E−6 | 2.40 | 1.09 |

***p < 0.001
**p < 0.01
*p < 0.05

TABLE 4

| Formula | n = | 72 hr Mean | SE | Ratio | rank | Flux (μg/hr * cm²) | SD | Lag time (hr) | SD | $k_p$ (cm/hr) | SD | D (cm²/hr) | SD | P | SD |
|---|---|---|---|---|---|---|---|---|---|---|---|---|---|---|---|
| G1 | 49 | 48.16 | 5.06 | 1.00 | 14 | 0.69 | 0.04 | −6.96 | 2.56 | 1.72E−5 | 1.00E−6 | −5.3E−5 | 1.4E−4 | −0.02 | 0.00 |
| G7 | 6 | 15.63 | 1.24 | 0.32 | 18 | 0.24 | 0.08 | 5.64 | 11.90 | 6.00E−6 | 1.88E−6 | 1.2E−5 | 3.5E−5 | 0.01 | 0.01 |
| G8 | 6 | 339.01 | 20.60 | 7.04* | 9 | 5.17 | 0.25 | −32.20 | 0.64 | 1.29E−4 | 6.29E−6 | −1.1E−5 | 5.7E−4 | −0.53 | 0.00 |
| G11 | 6 | 6165.16 | 409.69 | 128.01*** | 3 | 83.20 | 0.56 | −1.87 | 5.59 | 2.08E−3 | 1.40E−5 | 2.9E−5 | 7.6E−5 | 1.00 | 2.43 |

TABLE 4-continued

| For-mula | n = | 72 hr Mean | SE | Ratio | rank | Flux ($\mu$g/hr * cm$^2$) | SD | Lag time (hr) | SD | $k_p$ (cm/hr) | SD | D (cm$^2$/hr) | SD | P | SD |
|---|---|---|---|---|---|---|---|---|---|---|---|---|---|---|---|
| G12 | 6 | 3730.79 | 115.96 | 77.47*** | 5 | 67.04 | 3.08 | 581.20 | 105.48 | 1.68E − 3 | 7.71E − 5 | 6.3E − 7 | 3.5E − 6 | 124.35 | 1.04 |
| G14 | 6 | 21.60 | 2.65 | 0.45 | 17 | 0.37 | 0.11 | 13.23 | 6.17 | 9.25E − 6 | 2.75E − 6 | 5.4E − 5 | 6.9E − 5 | 0.02 | 0.01 |
| G15 | 6 | 28.36 | 2.62 | 0.59 | 16 | 0.60 | 0.16 | 22.84 | 4.31 | 1.50E − 5 | 4.00E − 6 | 2.3E − 5 | 5.6E − 6 | 0.04 | 0.02 |
| G16 | 10 | 7591.58 | 117.55 | 157.63*** | 1 | 127.99 | 6.29 | 947.79 | 128.59 | 3.20E − 3 | 1.57E − 4 | 3.9E − 7 | 2.9E − 6 | 387.15 | 2.58 |
| G18 | 5 | 5631.06 | 116.57 | 116.92*** | 4 | 47.87 | 5.72 | −46.56 | 15.06 | 1.20E − 3 | 1.43E − 4 | −9.9E − 6 | 6.2E − 6 | −7.03 | 2.47 |
| G19 | 6 | 41.68 | 1.43 | 0.87 | 15 | 0.71 | 0.08 | 13.73 | 5.15 | 1.78E − 5 | 2.00E − 6 | 2.8E − 5 | 1.1E − 5 | 0.03 | 0.01 |
| G20 | 5 | 58.78 | 7.27 | 1.22 | 13 | 1.22 | 0.35 | 24.80 | 2.34 | 3.05E − 5 | 8.75E − 6 | 1.2E − 5 | 2.0E − 6 | 0.11 | 0.03 |
| G21 | 5 | 820.31 | 89.14 | 17.03*** | 8 | 14.36 | 3.28 | 14.63 | 2.48 | 3.59E − 4 | 8.20E − 5 | 2.1E − 5 | 3.8E − 6 | 0.73 | 0.18 |
| G26 | 6 | 166.09 | 19.31 | 3.45 | 10 | 1.92 | 0.47 | −12.86 | 11.79 | 4.80E − 5 | 1.18E − 5 | −1.3E − 5 | 4.8E − 5 | −0.08 | 0.07 |
| G27 | 6 | 2475.31 | 200.21 | 51.40*** | 6 | 31.70 | 6.89 | 248.16 | 33.40 | 7.93E − 4 | 1.72E − 4 | 1.5E − 6 | 1.1E − 5 | 25.11 | 0.73 |
| G28 | 6 | 90.25 | 11.39 | 1.87 | 12 | 2.17 | 0.37 | 30.45 | 2.45 | 5.43E − 5 | 9.25E − 6 | 1.3E − 5 | 2.1E − 6 | 0.21 | 0.07 |
| G30 | 5 | 133.41 | 28.07 | 2.77 | 11 | 2.40 | 0.85 | 17.95 | 7.98 | 6.00E − 5 | 2.13E − 5 | 2.6E − 5 | 1.2E − 5 | 0.13 | 0.06 |
| G31 | 6 | 868.32 | 113.71 | 18.03*** | 7 | 9.53 | 4.09 | −23.58 | 16.25 | 2.38E − 4 | 1.02E − 4 | −4.1E − 5 | 3.5E − 5 | −0.48 | 0.21 |
| G32 | 6 | 7211.01 | 483.36 | 149.73*** | 2 | 74.11 | 19.36 | −20.96 | 11.96 | 1.85E − 3 | 4.84E − 4 | −2.2E − 5 | 1.8E − 5 | −5.60 | 3.71 |

***$p < 0.001$
**$p < 0.01$
*$p < 0.05$

TABLE 5

| Formula | | n size | 72 hr Mean | SE | rank | Flux ($\mu$g/hr * cm$^2$) | SD | Lag time (hr) | SD | $k_p$ (cm/hr) | SD | D (cm$^2$/hr) | SD | P | SD |
|---|---|---|---|---|---|---|---|---|---|---|---|---|---|---|---|
| G1 | 4% Piroxicam | 5 | 45.20 | 1.86 | 5 | 0.76 | 0.01 | −17.81 | 2.74 | 1.91E − 5 | 3.31E − 7 | −2.5E − 5 | 1.6E − 4 | −0.039 | 1.0E − 4 |
| G22 | 1% Piroxicam | 4 | 49.35 | 8.45 | 4 | 0.90 | 0.06 | −20.23 | 4.64 | 2.25E − 5 | 1.61E − 6 | −2.2E − 5 | 9.7E − 5 | −0.052 | 8.6E − 4 |
| G23 | 2% Piroxicam | 4 | 61.84 | 9.33 | 2 | 1.14 | 0.43 | −13.61 | 1.51 | 2.85E − 5 | 1.07E − 5 | −3.3E − 5 | 3.0E − 4 | −0.045 | 1.9E − 4 |
| G24 | 3% Piroxicam | 6 | 58.34 | 14.17 | 3 | 0.96 | 0.03 | −11.20 | 1.64 | 2.41E − 5 | 6.37E − 7 | −4.0E − 5 | 2.7E − 4 | −0.031 | 1.2E − 4 |
| G25 | 5% Piroxicam | 5 | 96.12 | 23.09 | 1 | 1.47 | 0.19 | −22.45 | 3.70 | 3.68E − 5 | 4.65E − 6 | −2.0E − 5 | 1.2E − 4 | −0.095 | 2.0E − 3 |

TABLE 6

| For-mula | n = | 72 hr Mean | SE | Ratio | rank | Flux ($\mu$g/hr * cm$^2$) | SD | Lag time (hr) | SD | $k_p$ (cm/hr) | SD | D (cm$^2$/hr) | SD | P | SD |
|---|---|---|---|---|---|---|---|---|---|---|---|---|---|---|---|
| G1 | 5 | 8.80 | 1.50 | 1.00 | 4 | 0.14 | 0.02 | −0.34 | 1.00 | 3.55E − 6 | 5.28E − 7 | −1.9E − 2 | 6.6E − 3 | −3.6E − 5 | 1.6E − 5 |
| G8 | 6 | 55.05 | 4.39 | 6.26** | 3 | 0.96 | 0.05 | −18.90 | 0.75 | 2.39E − 5 | 1.35E − 6 | −3.5E − 4 | 8.8E − 3 | −1.4E − 2 | 3.1E − 5 |
| G12 | 5 | 110.26 | 8.11 | 12.54*** | 2 | 1.89 | 0.16 | −5.30 | 0.50 | 4.72E − 5 | 4.07E − 6 | −1.2E − 3 | 1.3E − 2 | −7.5E − 3 | 6.1E − 5 |
| G16 | 5 | 161.35 | 16.62 | 18.35*** | 1 | 3.27 | 0.38 | −7.00 | 0.25 | 8.18E − 5 | 9.59E − 6 | −9.4E − 4 | 2.6E − 2 | −1.7E − 2 | 7.2E − 5 |

***$p < 0.001$
**$p < 0.01$
*$p < 0.05$

TABLE 7(A)

| Formula | Skin | n = | 72 hr ($\mu$g/ml) Mean | SE | Ratio | Rank | Flux ($\mu$g/hr * cm$^2$) | SD | Lag time (hr) | SD |
|---|---|---|---|---|---|---|---|---|---|---|
| G1 | human | 5 | 8.80 | 1.49 | 1.00 | 3 | 0.14 | 0.02 | −0.34 | 1.00 |
|  | rabbit | 49 | 48.16 | 5.06 | 5.48 | 2 | 0.69 | 0.04 | −6.96 | 2.56 |
|  | nude mice | 52 | 259.34 | 15.31 | 29.49 | 1 | 1.18 | 0.57 | −1.71 | 0.65 |
| G8 | human | 6 | 55.05 | 4.39 | 1.00 | 3 | 0.96 | 0.02 | −18.90 | 1.00 |
|  | rabbit | 6 | 339.01 | 20.60 | 6.16 | 2 | 5.17 | 0.25 | −32.20 | 0.64 |
|  | nude mice | 5 | 873.60 | 78.01 | 15.87 | 1 | 13.28 | 1.23 | −27.24 | 8.57 |
| G12 | human | 5 | 110.26 | 8.11 | 1.00 | 3 | 1.89 | 0.16 | −5.30 | 0.50 |
|  | rabbit | 6 | 3730.79 | 115.96 | 33.84 | 2 | 67.04 | 3.08 | 581.20 | 105.48 |
|  | nude mice | 6 | 5846.85 | 171.25 | 53.03 | 1 | 70.72 | 2.35 | 563.63 | 0.36 |
| G16 | human | 5 | 161.35 | 16.62 | 1.00 | 3 | 3.27 | 0.38 | −7.00 | 0.25 |
|  | rabbit | 6 | 7591.58 | 117.55 | 47.05 | 1 | 127.99 | 6.29 | 947.79 | 128.59 |
|  | nude mice | 5 | 7160.11 | 371.56 | 44.38 | 2 | 77.97 | 14.91 | −21.08 | 8.41 |

| Formula | Skin | n = | $k_p$ (cm/hr) | SD | D (cm$^2$/hr) | SD | P | SD |
|---|---|---|---|---|---|---|---|---|
| G1 | human | 5 | 3.5E − 6 | 5.3E − 7 | −1.9E − 2 | 6.6E − 3 | −3.6E − 5 | 1.6E − 5 |
|  | rabbit | 49 | 1.7E − 5 | 1.0E − 6 | −5.3E − 5 | 1.4E − 4 | −1.5E − 2 | 3.3E − 4 |
|  | nude mice | 52 | 3.0E − 5 | 1.4E − 5 | −6.1E − 5 | 1.6E − 4 | −1.2E − 2 | 2.2E − 3 |
| G8 | human | 6 | 2.4E − 5 | 5.3E − 7 | −3.5E − 4 | 6.6E − 3 | −1.4E − 2 | 1.6E − 5 |
|  | rabbit | 6 | 1.3E − 4 | 6.3E − 6 | −1.1E − 5 | 5.7E − 4 | −5.3E − 1 | 5.2E − 4 |
|  | nude mice | 5 | 3.3E − 4 | 3.1E − 5 | −3.8E − 6 | 1.2E − 5 | −2.2E + 0 | 6.3E − 2 |
| G12 | human | 5 | 4.7E − 5 | 4.1E − 6 | −1.2E − 3 | 1.3E − 2 | −7.5E − 3 | 6.1E − 5 |
|  | rabbit | 6 | 1.7E − 3 | 7.7E − 5 | 6.3E − 7 | 3.5E − 6 | 1.2E + 2 | 1.0E + 0 |
|  | nude mice | 6 | 1.8E − 3 | 5.9E − 5 | 1.8E − 7 | 2.9E − 4 | 2.4E + 2 | 5.1E − 3 |
| G16 | human | 5 | 8.2E − 5 | 9.6E − 6 | −9.4E − 4 | 2.6E − 2 | −1.7E − 2 | 7.2E − 5 |
|  | rabbit | 6 | 3.2E − 3 | 1.6E − 4 | 3.9E − 7 | 2.9E − 6 | 3.9E + 2 | 2.6E + 0 |
|  | nude mice | 5 | 1.9E − 3 | 3.7E − 4 | −6.6E − 6 | 3.2E − 6 | −9.1E + 0 | 3.8E + 0 |

TABLE 7(B)

| Formula | Skin | n = | 72 hr ($\mu$g/ml) Mean | SE | Ratio | Rank | Flux ($\mu$g/hr * cm$^2$) | SD | Lag time (hr) | SD |
|---|---|---|---|---|---|---|---|---|---|---|
| G1 | human | 4 | 113.36 | 4.00 | 1.00 | 1 | 0.85 | 0.07 | 53.18 | 12.27 |
|  | rabbit | 5 | 55.44 | 18.20 | 0.49 | 2 | 0.68 | 0.03 | −0.27 | 0.02 |
| G16 | human | 4 | 651.97 | 93.00 | 1.00 | 2 | 9.04 | 2.33 | −70.67 | 21.49 |
|  | rabbit | 4 | 9219.14 | 1273.50 | 14.14 | 1 | 134.45 | 25.94 | −458.58 | 67.39 |

| Formula | Skin | n = | $k_p$ (cm/hr) | SD | D (cm$^2$/hr) | SD | P | SD |
|---|---|---|---|---|---|---|---|---|
| G1 | human | 5 | 2.13E − 5 | 1.63E − 6 | 1.2E − 4 | 5.4E − 4 | 3.4E − 2 | 6.0E − 4 |
|  | rabbit | 5 | 1.70E − 5 | 8.50E − 7 | −1.5E − 3 | 1.8E − 2 | −5.6E − 4 | 2.3E − 6 |
| G16 | human | 4 | 2.3E − 4 | 5.8E − 5 | −5.7E − 6 | 3.1E − 4 | −7.94 | 0.04 |
|  | rabbit | 4 | 3.36E − 3 | 6.49E − 4 | −8.7E − 7 | 5.9E − 6 | −188.74 | 5.35 |

TABLE 8

| Drug | Formula | n = | 72 hr (ug/ml) Mean | SE | Ratio | Rank | Flux ($\mu$g/hr * cm$^2$0 | SD | Lag time (hr) | SD |
|---|---|---|---|---|---|---|---|---|---|---|
| Piroxicam | G1 | 3 | 79.74 | 21.26 | 1.00 | 2 | 1.20 | 0.52 | 8.49 | 4.96 |
|  | G16 | 5 | 6472.80 | 341.95 | 81.17 | 1*** | 93.65 | 9.92 | 4.75 | 5.34 |
| Isoxicam | G1 | 5 | 372.79 | 53.01 | 1.00 | 2 | 5.33 | 1.52 | 10.95 | 1.52 |
|  | G16 | 5 | 6928.93 | 249.39 | 18.59 | 1*** | 109.21 | 12.13 | 3.01 | 2.43 |
| Tenoxicam | G1 | 5 | 84.33 | 23.96 | 1.00 | 2 | 0.82 | 0.38 | 25.72 | 25.32 |
|  | G16 | 4 | 7276.48 | 361.33 | 86.29 | 1*** | 118.99 | 20.39 | 9.81 | 2.05 |

TABLE 8-continued

| Drug | Formula | n = | $k_p$ (cm/hr) | SD | D (cm²/hr) | SD | P | SD |
|---|---|---|---|---|---|---|---|---|
| Piroxicam | G1 | 3 | 3.0E − 5 | 1.3E − 5 | 3.9E − 5 | 2.4E − 5 | 0.047 | 0.048 |
| | G16 | 5 | 2.3E − 3 | 2.5E − 4 | 1.6E − 5 | 1.6E − 4 | 1.600 | 1.814 |
| Isoxicam | G1 | 5 | 1.3E − 4 | 3.8E − 5 | 5.6E − 5 | 1.3E − 5 | 0.146 | 0.048 |
| | G16 | 5 | 2.7E − 3 | 3.0E − 4 | −5.2E − 5 | 4.5E − 4 | 0.912 | 0.789 |
| Tenoxicam | G1 | 5 | 2.1E − 5 | 9.6E − 6 | 6.0E − 5 | 1.0E − 4 | 0.056 | 0.032 |
| | G16 | 4 | 3.0E − 3 | 5.1E − 4 | 4.4E − 5 | 2.4E − 5 | 3.750 | 1.297 |

***$p < 0.0001$

We claim:

1. A transdermal preparation for the delivery of a therapeutically effective amount of an oxicam to the systemic circulation of a mammal, said composition comprising:

0.1% to 50% of an oxicam, 0.1% to 70% of an absorption enhancer which is a member selected from the group consisting of oleanolic acid, trans-cinnamic acid, glycyrrhizin, β-myrcene, trans-cinnamaldehyde, cineole, betulin, terpineol, epicatechin, ergosterol, terphenyl, pinene, limonene, digitonin, ursolic acid and combinations thereof, and 0.01 to 99.8% of a pharmaceutically acceptable excipient.

2. The transdermal preparation according to claim 1 wherein the oxicam is a member selected from the group consisting of isoxicam, sudoxicam, cinnoxicam, tenoxicam, lomoxicam and piroxicam.

3. The transdermal preparation according to claim 1 wherein the excipient is a member selected from the group consisting of sodium carboxymethylcellulose and ethylene glycol and combinations thereof.

4. The transdermal preparation according to claim 1 further comprising Tween 80.

5. The transdermal preparation according to claim 1 further comprising ethyl myristate.

6. The transdermal preparation according to claim 1 further comprising lauryl alcohol.

7. The transdermal preparation according to claim 1 in the form of an ointment, suspension, gel, solution, aerosol, paste or a patch.

8. A method for the treatment of inflamation comprising:

applying to the skin of a mammal in need thereof, an effective amount of the transdermal preparation of claim 1.

9. A method for the treatment of pain comprising:

applying to the skin of a mammal in need thereof, an effective amount of the transdermal preparation of claim 1.

10. A method for antipyretic treatment comprising:

applying to the skin of a mammal in need thereof, an effective amount of the transdermal preparation of claim 1.

11. A transdermal delivery preparation effective in producing effects of relieving fever and pain or inflammation, comprising 0.1–50% oxicam having the effect of relieving fever, pain or inflamation, 0.1–70% of a penetration enhancer component which is derived from Chinese herbs, and an excipient thereby enabling penetrating into the skin by said preparation.

12. A transdermal delivery preparation according to claim 11, wherein said oxicam analgesic, effective in relieving inflamation and fever, is a member selected from the group consisting of isoxicam, sudoxicam, cinnoxicam, tenoxicam, lomoxicam and piroxicam.

13. A transdermal delivery preparation according to claim 11, wherein said penetration enhancer is a member selected from the group consisting of oleanolic acid, trans-cinnamic acid, glycyrrhizin, β-myrcene, trans-cinnamaldehyde, cineole, betulin, terpineol, epicatechin, ergosterol, terphenyl, pinene, limonene, digitonin, ethyl myristate and ursolic acid and the surfactant, Tween 80.

14. A transdermal delivery preparation according to claim 11, wherein the excipient is in the range of 0.01–99.5% and is ethylene glycol or sodium carboxymethylcellulose.

15. A transdermal delivery preparation comprising 0.1–50% piroxicam, and a penetration enhancer effective in relieving inflammation and fever which is a member selected from the group consisting of oleanolic acid, trans-cinnamic acid, glycyrrhizin, β-myrcene, trans-cinnamaldehyde, cineole, betulin, terpineol, epicatechin, ergosterol, terphenyl, pinene, limonene, digitonin, ethyl myristate and ursolic acid and the surfactant, Tween 80.

16. A transdermal delivery preparation according to claim 11 in the form of an ointment, suspension, gel, solution, aerosol, paste, or a patch.

* * * * *